US011009511B2

(12) United States Patent
Snoeck et al.

(10) Patent No.: US 11,009,511 B2
(45) Date of Patent: May 18, 2021

(54) METHODS FOR DETECTING AND/OR MEASURING ANTI-DRUG ANTIBODIES, IN PARTICULAR TREATMENT-EMERGENT ANTI-DRUG ANTIBODIES

(71) Applicant: Ablynx N.V., Zwijnaarde (BE)

(72) Inventors: Veerle Snoeck, Zingem (BE); Marie-Ange Buyse, Merelbeke (BE); Judith Baumeister, Mechelen (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 640 days.

(21) Appl. No.: 15/311,645

(22) PCT Filed: May 13, 2015

(86) PCT No.: PCT/EP2015/060671
§ 371 (c)(1),
(2) Date: Nov. 16, 2016

(87) PCT Pub. No.: WO2015/173342
PCT Pub. Date: Nov. 19, 2015

(65) Prior Publication Data
US 2017/0082637 A1  Mar. 23, 2017

Related U.S. Application Data

(60) Provisional application No. 61/994,472, filed on May 16, 2014.

(51) Int. Cl.
*G01N 31/00* (2006.01)
*G01N 33/53* (2006.01)
*G01N 33/68* (2006.01)
*G01N 33/94* (2006.01)

(52) U.S. Cl.
CPC ..... *G01N 33/6854* (2013.01); *G01N 33/6857* (2013.01); *G01N 33/94* (2013.01)

(58) Field of Classification Search
None
See application file for complete search history.

(56) References Cited

FOREIGN PATENT DOCUMENTS

| WO | WO-2006122786 A2 * | 11/2006 | ............ A61P 25/08 |
|---|---|---|---|
| WO | WO 2011/075861 A1 | 6/2011 | |
| WO | WO 2012/175741 A2 | 12/2012 | |
| WO | WO-2012175741 A2 * | 12/2012 | ............ C07K 16/00 |
| WO | WO 2013/024059 A2 | 2/2013 | |

OTHER PUBLICATIONS

Tascilar et al. (Annals of Oncology 10,Suppl. 4:S107-S110, 1999).*
Tockman et al. (Cancer Research 52:2711s-2718s, 1992).*
Tascilar et al. (Annals of Oncology 10.Suppl. 4:S107-S110, 1999) (Year: 1999).*
Tascilar et al. (Annals of Oncoloav IO.Suddl. 4:S107-S110, 1999) (Year: 1999).*
Tockman etal. (Cancer Research 52:2711s-2718s, 1992) (Year: 1992).*
Edwards etal. (Journal of Molecular Biology, vol. 334, pp. 103-118, 2003) (Year: 2003).*
Goel etal. (The Journal of Immunology, vol. 173 (12), pp. 7358-7367, 2004) (Year: 2004).*
PCT/EP2015/060671, Jul. 22, 2015, International Search Report and Written Opinion.
PCT/EP2015/060671, Aug. 3, 2016, International Preliminary Report on Patentability.
Xue et al., Pre-existing biotherapeutic-reactive antibodies: survey results within the American Association of Pharmaceutical Scientists. AAPS J. Jul. 2013;15(3):852-5. doi: 10.1208/s12248-013-9492-4.
Muyldermans et al., Recognition of antigens by single-domain antibody fragments: the superfluous luxury of paired domains. Trends Biochem Sci. Apr. 2001;26(4):230-5.
Muyldermans et al., Unique single-domain antigen binding fragments derived from naturally occurring camel heavy-chain antibodies. J Mol Recognit. Mar.-Apr. 1999;12(2):131-40.
Riechmann et al., Single domain antibodies: comparison of camel VH and camelised human VH domains. J Immunol Methods. Dec. 10, 1999;231(1-2):25-38.
Muyldermans, Single domain camel antibodies: current status. J Biotechnol. Jun. 2001;74(4):277-302. doi: 10.1016/s1389-0352(01)00021-6.
Roitt et al., Immunology. Chapter 5: Molecules which Recognize Antigen. Second Edition. Gower Medical Publishing. London. 1989. 5.1-5.11. 14 pages.

* cited by examiner

*Primary Examiner* — Lisa V Cook
(74) *Attorney, Agent, or Firm* — Wolf, Greenfield & Sacks, P.C.

(57) ABSTRACT

Described herein are methods, assays and techniques for detecting and/or measuring anti-drug antibodies that bind to a protein, polypeptide or other compound or molecule that comprises at least one immunoglobulin variable domain with an exposed C-terminal region.

7 Claims, 12 Drawing Sheets
Specification includes a Sequence Listing.

Figure 5

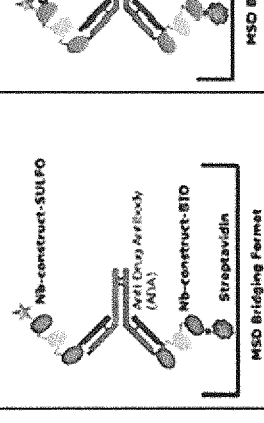

| | Homogeneous ECL-based bridging | Homogeneous modified ECL-based bridging | Sequential ECL-based bridging | Sequential ELISA-based bridging | Direct ELISA format |
|---|---|---|---|---|---|
| Assay set-up | MSD Bridging Format | MSD Bridging Format | MSD Bridging Format | ELISA Bridging Format | ELISA direct Format |
| Capture Antigen | Biotinylated Nanobody construct | Biotinylated Nanobody construct | Biotinylated Nanobody construct | Nanobody construct | Nanobody construct |
| Detection reagent | Sulfo-tagged Nanobody construct | Sulfo-tagged Nanobody construct-Ala (one additional Alanine at the C-terminal end of the authentic Nanobody construct) | Sulfo-tagged Nanobody construct | Biotinylated Nanobody construct & HRP conjugated Streptavidin and TMB | HRP conjugated goat anti-hIgG Fcγ specific and Western Lightning ECL pro |
| Detection instrument | MSD Sector Imager 2400 | MSD Sector Imager 2400 | MSD Sector Imager 2400 | Microtitre plate reader | Perkin Elmer |
| Positive control | anti-Nanobody construct rabbit serum (P01 rabbit anti-sera supplied by Pfizer Inc-Wyeth Research) | anti-Nanobody construct rabbit serum (P01 rabbit anti-sera supplied by Pfizer Inc-Wyeth Research) | anti-Nanobody construct rabbit serum (P01 rabbit anti-sera supplied by Pfizer Inc-Wyeth Research) | anti-Nanobody construct rabbit serum (P01 rabbit anti-sera supplied by Pfizer Inc-Wyeth Research) | anti-Nanobody construct rabbit serum (P01 rabbit anti-sera supplied by Pfizer Inc-Wyeth Research) |
| MRD | 50 (25 → ½ in master mix) | 50 (25 → ½ in master mix) | 25 | 25 | 100 |

Figure 5 (continued)

| | Homogeneous ECL-based bridging | Homogeneous modified ECL-based bridging | Sequential ECL-based bridging | Sequential ELISA-based bridging | Direct ELISA format |
|---|---|---|---|---|---|
| Assay set-up | MSD Bridging Format | MSD Bridging Format | MSD Bridging Format | ELISA Bridging Format | ELISA direct Format |
| Sensitivity | 1/182.250 – 1/60.750 (= 70 - 200 ng/mL estimated based on 10 mg/mL total Ig and 5% Nanobody construct specific) | 1/182.250 – 1/60.750 (=70 - 200 ng/mL estimated based on 10 mg/mL total Ig and 5% Nanobody construct specific) | 1/2.250 (=5.5 µg/mL estimated based on 10 mg/mL total Ig and 5% Nanobody construct specific) | 1/20.250 (=600 ng/mL estimated based on 10 mg/mL total Ig and 5% Nanobody construct specific) | 1/20.250 (=600 ng/mL estimated based on 10 mg/mL total Ig and 5% Nanobody construct specific). Note that estimate is based on rabbit serum and HRP-conjugated anti-rabbit-IgG detector. |
| Cut-point setting remarks | Cut-point setting is arbitrary. Commonly used statistical methods are not applicable | possible | possible | Cut-point setting is arbitrary. Commonly used statistical methods are not applicable | Cut-point setting is arbitrary. Commonly used statistical methods are not applicable |
| Detection of positive control in presence of interference | Not possible | Only samples with high interference might defy detection of low ADA levels (ng range) | Samples with high interference might defy detection of high ADA levels (µg range) | Not possible | Technically not feasible (due to different detection reagents for rabbit-positive control and interference) |
| Conclusion | impacted by interference | Allows for detection of ADA in the presence of interference | Impacted by interference | Impacted by interference | Impacted by interference |

METHODS FOR DETECTING AND/OR MEASURING ANTI-DRUG ANTIBODIES, IN PARTICULAR TREATMENT-EMERGENT ANTI-DRUG ANTIBODIES

RELATED APPLICATIONS

This application is a national stage filing under 35 U.S.C. § 371 of International Application No. PCT/EP2015/060671, filed May 13, 2015, which was published under PCT Article 21(2) in English, and claims the benefit under 35 U.S.C. § 119(e) of U.S. provisional application Ser. No. 61/994,472, filed May 16, 2014, the entire contents of each of which is incorporated by reference herein in its entirety.

The present invention relates to methods, assays and techniques for detecting and/or measuring anti-drug antibodies (ADA's), and in particular treatment-emergent ADA's.

In particular, present invention relates to methods, assays and techniques for detecting and/or measuring ADA's (and in particular treatment-emergent ADA's) against proteins, polypeptides or other (biological) compounds or molecules that comprise at least one immunoglobulin variable domain (as further described herein), and in particular at least one immunoglobulin single variable domain (as further described herein).

More in particular, the methods, assays and techniques of the invention can be used for detecting and/or measuring ADA's (and in particular treatment-emergent ADA's) against proteins, polypeptides or other (biological) compounds or molecules that comprise at least one immunoglobulin variable domain (and in particular at least one immunoglobulin single variable domain or "ISV/ISVD") that has an exposed C-terminal region (as further described herein), even more in particular where such exposed C-terminal region may be bound by "pre-existing antibodies" (as further described herein) that are (or may be) present in the sample to be tested (or where there is a risk that the sample tested contains such pre-existing antibodies or other interfering factors).

More generally, the methods, assays and techniques of the invention can be used for detecting and/or measuring ADA's (and in particular treatment-emergent ADA's) against such proteins, polypeptides or other (biological) compounds or molecules where the sample to be tested contains (or may contain and/or where there is a risk that such sample contains) one or more pre-existing antibodies (or other pre-existing interfering factors) that can affect the reliability of the assay, for example such that the assay cannot be used (or cannot reliably be used) to measure "true" ADA's (i.e. "treatment-emergent" ADA's) and/or to distinguish between "true" and/or treatment-emergent ADA's on the one hand and any such pre-existing antibodies (or other interfering factors including pre-existing interfering factors) present in the sample on the other hand.

As further described herein, the methods, assays and techniques of the invention can in particular be used for detecting and/or measuring ADA's in a sample (such as a blood sample or another biological sample as mentioned herein) that has been obtained from a (human) subject to whom such a protein, polypeptide, compound or molecule has been administered. For example, where the protein, polypeptide, compound or molecule is a (biological) drug or therapeutic, such sample may have been obtained from a patient who has been treated with such a protein, polypeptide, compound or molecule (in particular where the treatment used carries a risk that ADA's against the protein, polypeptide, compound or molecule may emerge, and/or where it is desirable to monitor whether any ADA's emerge as a result of such treatment); or from a subject to whom such a protein, polypeptide, compound or molecule has been administered as part of a clinical trial (where again it may be desirable or even required to monitor whether any ADA's against the protein, polypeptide, compound or molecule emerge). In this respect, it will be clear to the skilled person that (the emergence and/or the levels of) certain treatment-emergent ADA's may influence or affect the pharmacological properties of a protein drug (such as its pharmacokinetics, clearance or even efficacy) may influence or affect the therapeutic efficacy of treatment with the protein drug (and/or the treatment regime used), and/or may be a factor for the treating physician in taking decisions relating to the treatment or the treatment regimen (for example, increase the dose or to switch the patient to another drug or treatment); and that accordingly, there is a constant need in the art for improved methods and techniques for detecting or measuring ADA's, as now provided by the present invention.

Further aspects, embodiments, applications, uses and advantages of the present invention will become clear from the further description herein.

Throughout the present application and appended claims, each time reference is made to a "protein, polypeptide or other compound or molecule" (also collectively referred to herein as a "biologic"), such protein, polypeptide or other compound or molecule may in particular be (and according to one aspect of the invention, preferably is) a drug or therapeutic. Such a drug or therapeutic may for example, after administration to a human subject (such as a patient in need of treatment with the drug or therapeutic), be capable of interacting with and/or modulating a therapeutically relevant target, pathway or other interaction within the human body. For example, for this purpose, the protein, polypeptide or other compound or molecule may contain one or more binding units or binding domains (such as, for example and without limitation, one or more immunoglobulin variable domains and in particular one or more immunoglobulin single variable domain such as one or more nanobodies) that are directed against, capable of (specifically) binding to, interacting with and/or modulating such a therapeutic target, pathway or interaction. Examples of the same will be clear to the skilled person based on the disclosure herein and the further prior art cited herein.

Throughout the present application and appended claims, each time reference is made to a "protein, polypeptide or other compound or molecule", such "other compound or molecule" is preferably a biological compound or molecule (including, without limitation, any biological complexes).

Also, throughout the specification, the abbreviations "ISV" and "ISVD" are interchangeably used to indicate immunoglobulin single variable domains (as further defined herein). Furthermore, throughout the specification, when a method, aspect, feature or element of the invention is said to be "as further described herein", this should generally be understood as meaning that any preference(s) that are generally described herein for (the methods of) the invention are also preferences for such a method, aspect, feature or element, unless the specific context requires otherwise.

There have been several reports in the prior art of (often pre-existing) proteins or factors that may be present in biological samples obtained from human subjects (such as blood samples, serum samples or other biological fluids or samples) and that apparently can bind to the C-terminal region of immunoglobulin variable domains where such C-terminal region is exposed (i.e. where this C-terminal region is not shielded or covered by another part of the protein or polypeptide of which said immunoglobulin variable domain forms a part. In this respect, it should be noted that in a conventional four-chain antibody, the C-terminal regions of the variable domains are generally shielded by the constant domains to which said variable domains are linked). For example, it is described in WO12/175741 that the C-terminal region of an VH domain, when exposed (as defined herein and in WO12/175741), is part of a putative epitope on the VH domain that also includes, among other residues, the amino acid residue at position 14 (and the amino acid residues next/close to the same in the amino acid sequence, such as positions 11, 13 and 15) and may also comprise the amino acid residue at position 83 (and the amino acid residues next/close to the same in the amino acid sequence, such as positions 82, 82a, 82b and 84) and/or the amino acid residue at position 108 (and the amino acid residues next/close to the same in the amino 30 acid sequence, such as positions 107. As in WO12/17574, this putative epitope is also collectively referred to herein as the "C-terminal region", it being understood that this C-terminal region at least comprises the C terminal sequence VTVSS (i.e. each of positions 109, 110, 111, 112 and 113) and the amino acid residue at position 14, and may also comprise the amino acid residues at positions 83 and 108, and possibly also the amino acid residues at positions 13, 15, 82b, 83, 84 and 107.

It has also been described in the art that this epitope constitutes a hydrophobic patch that in a conventional full-sized antibody is buried in the interface between the variable domain and the constant domain but that becomes solvent-exposed when the variable domain is not associated with a constant domain (see for example Nieba et al., Protein Engineering, 10, 435-444 (1997) and Harmsen et al., Molecular Immunology (2000), 579-590).

It is also well known that such "buried" epitopes (also referred to in the art as "neo-epitopes" or "cryptic epitopes") may trigger the immune system once they become solvent-exposed, for example due to degradation, misfolding or aggregation of the protein involved. For example, in the case of buried hydrophobic portions of biomolecules (so-called "hyppos"), it has been suggested that these form part of a general damage-associated molecular pattern that leads to innate immune responses once the hyppos become solvent-exposed (see for example Seong and Matzinger, Nature Reviews 2004, 469), and various examples of previously-buried hydrophobic patches triggering immune responses have been described in the art (see for example David et al., JBC, 2001, 6370-6377; Matsuura et al., International Immunology, 2000, 1183-1192; Rasheed et al., Life Sciences 79 (2000), 2320-2328). More generally, it is also known in the art that hydrophobic amino acids are prone to be part of B-cell epitopes (see for example WO11/07586, page 10; and Kolaskar, FEBS 276, 172-174 (1990)). Similarly, it has been described that the hydrophobic patch at the C-terminus of a heavy-chain variable domain (as described by Nieba et al. and Harmsen et al., supra) may form B-cell epitopes which can give rise to and/or interact with (emerging and/or pre-existing) anti-drug antibodies (WO11/07586). For this reason, it has been proposed to make mutations to some of the amino acid residues that form part of the C-terminus of the variable domains to reduce hydrophobicity and/or to remove B-cell epitopes. For example, Nieba et al. suggest to mutate positions 11, 14, 41, 84, 87 and/or 89 of a VH region (numbering according to Kabat), whereas in WO11/07586 it is suggested to mutate positions 99, 101 and/or 148 (AHo numbering) of a VL domain or positions 12, 97, 98, 99, 103 and/or 144 of a VH domain (again AHo numbering—these positions correspond to positions 11, 83, 84, 85, 89 and 103 according to Kabat). Similarly, Harmsen et al. suggest to mutate positions 12 and 101 (1MGT numbering; these are positions 11 and 89 according to Kabat) to compensate for the absence of a $C_H1$ domain; and they also identify a specific subfamily of VHH's (called "VHH4's") that contain amino acids that are suitable candidates for substitutions at these positions.

It has also been described in the art (see for example WO12/175741 and the references cited in the next paragraphs) that biological samples obtained from human subjects may contain (pre-existing) proteins or factors that are capable of binding to the exposed C-terminal region/end of an immunoglobulin variable domain (for example, the C-terminal region or end of an ISVD or of a VH or VL domain in an ScFv or diabody). For example, WO2013/024059 states that "in sera from some healthy naive human subjects, pre-existing anti-VH autoantibodies are present that can bind both VH domain antibodies and VHH molecules, as well as anti-VL (eg V kappa (VK)) autoantibodies that can bind VL molecules.", and that "the pre-existing ADAs that bind VH dAbs are similar to anti-hinge antibodies in that they bind IgG fragments but not those same sequences found in situ on intact IgG."

Holland et al., J. Clin. Immunol. 2013, 33(7):1192-203 describe that the blood of around half of normal healthy humans contain varying levels of a new class of anti-IgG autoantibodies that can bind to the framework sequences of fully human $V_H$ domain antibodies (which Holland et al. also refer to as "HAVH auto-antibodies"). Holland et al. further mention that these auto-antibodies appear to be predominantly of the IgG isotype, display a relatively high affinity (about $10^{-10}$M) affinity for $V_H$ sequences, and that a free C-terminus appears to be important for the binding of these HAVH autoantibodies to $V_H$ domains.

WO12/175741 also describes that such pre-existing antibodies or other (pre-existing) factors may interfere with ADA assays. This is also generally referred to as "protein interference" in WO12/175741, and the pre-existing antibodies or other factors that (may) interfere with the assays are also referred to generally in WO12/175741 as "interference factors".

The issues relating to pre-existing biotherapeutic-reactive antibodies against biotherapeutic molecules and their regulatory impact are also generally discussed by Xue et al., AAPS J. 2013; 15(3):852-5.

The aforementioned prior art has also focused on ways in which the sequence of an immunoglobulin variable domain may be modified so as to prevent or reduce binding of such pre-existing antibodies/factor(s) to the variable domains. In this respect, WO2011/07586 suggests to make one or more mutations in the amino acid sequence of the variable domain at some specific positions of the domain (which positions are surface-exposed). WO12/175741 describes that the binding of such pre-existing antibodies/factors may be reduced by adding a few amino acid residues (and as little as one alanine residue) to the C-terminal end of the VH-domain and/or by making one or more specific substitutions or deletions within the C-terminal region of the variable domain, which is described in WO12/175741 as at least comprising the C-terminal amino acid sequence VTVSS and the amino acid residue at position 14 (for which position WO12/175741 teaches that the presence of an alanine residue provides for reduced binding of pre-existing antibodies as compared to the presence of the "human" amino acid residue proline), and possibly also the amino acid residues at positions 108 and 83 and amino acid residues close to said positions (WO2013/024059 provides essentially the same teaching as WO12/175741).

For example, in research performed by applicant/assignee leading up to the filing of WO 12/175741, it has been found that adding a single alanine residue to the C-terminal region or end of an exposed VH domain in will usually prevent/remove (essentially all of) the binding of pre-existing antibodies/factors that are present in samples obtained from most human subjects (see for example page 62, lines 20-25 and page 57, line 30 to page 58, lines 3 of WO12/175741); and these findings have been confirmed by additional results that were obtained by applicant/assignee after the filing of WO12/175741 when the C-terminal alanine substitution of WO12/175741 was applied to other Nanobodies (data not shown).

Although the present invention is not limited to any explanation or hypothesis regarding the nature of the protein (s) or factor(s) that may be present in human samples and that can bind to the free C-terminus of immunoglobulin variable domains (and in particular of VH-based variable domains), it would appear that the interfering protein(s) or factor(s) are likely pre-existing and not treatment-emergent, and is likely to be a (polyclonal) antibody, and in particular, an IgG. Accordingly, in the further description herein, the interference/interfering factor(s) as described in WO12/175741 will also be referred to herein as "pre-existing antibodies". So as used herein, the term "(pre-existing) interfering factor" in particular refers to such pre-existing antibodies, but in its broadest sense does not exclude other proteins, polypeptides or factors that may be present in the blood or serum of human subjects/patients and that can interfere with ADA assays in essentially a similar manner as described herein.

The aforementioned prior art has also focused on ways in which the sequence of an immunoglobulin variable domain may be modified so as to prevent or reduce binding of such pre-existing antibodies/factor(s) to the variable domains. In this respect, WO2011/07586 suggests to make one or more mutations in the amino acid sequence of the variable domain at some specific positions of the domain (which positions are surface-exposed). WO12/175741 describes that the binding of such pre-existing antibodies/factors may be reduced by adding a few amino acid residues (and as little as one alanine residue) to the C-terminal end of the VH-domain and/or by making one or more specific substitutions or deletions within the C-terminal region of the variable domain, which is described in WO12/175741 as at least comprising the C-terminal amino acid sequence VTVSS and the amino acid residue at position 14 (for which position WO12/175741 teaches that the presence of an alanine residue provides for reduced binding of pre-existing antibodies as compared to the presence of the "human" amino acid residue proline), and possibly also the amino acid residues at positions 108 and 83 and amino acid residues close to said positions (WO2013/024059 provides essentially the same teaching as WO12/175741).

For example, in research performed by applicant/assignee leading up to the filing of WO 12/175741, it has been found that adding a single alanine residue to the C-terminal region or end of an exposed VH domain in will usually prevent/remove (essentially all of) the binding of pre-existing antibodies/factors that are present in samples obtained from most human subjects (see for example page 62, lines 20-25 and page 57, line 30 to page 58, lines 3 of WO12/175741); and these findings have been confirmed by additional results that were obtained by applicant/assignee after the filing of WO12/175741 when the C-terminal alanine substitution of WO12/175741 was applied to other Nanobodies (data not shown).

Also, in WO12/175741 as well as in WO12/175400 by applicant/assignee, the C-terminal extensions described in WO12/175741 are applied to certain serum-albumin-binding Nanobodies (see for example WO12/175741: SEQ ID NO's: 37, 51-53 and 55-64 and the constructs shown in SEQ ID NO's: 41, 43 and 44; and WO12/175400: SEQ ID NO's: 6 to 11).

Other examples of Nanobodies and other immunoglobulin single variable domains that have C-terminal extensions and/or mutations in the C-terminal region can for example be found in the following prior art: WO06/129843 (see for example SEQ ID NO's: 4, 6, 8 and 10); WO 03/035695 (see for example some of the sequences listed on pages 61-64); Vu et al., Molecular Immunology, 1121-1131, 1997 (see for example some of the sequences listed in FIG. 2); WO 11/003622 (see for example the sequences given as SEQ ID NO's: 10 to 27); WO09/058383 (see for example the sequence TAR2h-10-27 mentioned on page 51); WO10/042815 (see for example the sequences of SEQ ID NO's: 15, 17, 27 and 30); and WO04/044204 (see for example the sequences of SEQ ID NO's: 31, 35, 37, 47 and 49).

Nevertheless, and irrespective of the nature of the interfering factor(s), the problem remains that the presence of such interfering factor(s) in the sample tested may interfere with the detection and/or measurement of (drug-specific, and in particular treatment-emergent) ADA's in ADA assays, in particular where the ADA assay is used to detect or measure ADA's against a protein, polypeptide or other compound or molecule that comprises at least one immunoglobulin variable domain (such as an immunoglobulin single variable domain) with an exposed C-terminal region (for example, because said immunoglobulin variable domain is present at and/or forms the C-terminal region of the protein, polypeptide or other compound or molecule). In addition, it may be useful to classify binding antibodies as (likely) treatment emergent antibodies or (likely) pre-existing antibodies as the two forms may exert distinct immunological profiles.

The invention addresses this problem by providing an ADA assay that can be used to measure or determine "true" ADA's (i.e. drug-specific ADA's, and in particular treatment-emergent ADA's) in samples that comprise (or may comprise or are suspected to comprise) interfering factor(s), and in particular interfering factors of the kind referred to in the prior art described above.

As further described herein, the ADA assay of the invention (which is a modification of a bridging assay format known per se from the prior art, and can in particular be a modification of a known electrochemiluminescence assay format known per se from the prior art) can be used to detect or measure ADA's in a suitable sample against any protein, polypeptide or other compound or molecule that comprises at least one immunoglobulin variable domain, but can in particular be used to detect or measure ADA's in a suitable sample against a protein, polypeptide or other compound or molecule that comprises at least one immunoglobulin variable domain with an exposed C-terminal region (as further described herein).

As also further described herein, according to one specific aspect of the invention, the ADA assay described herein can be used to detect or measure ADA's in a suitable sample against a protein, polypeptide or other compound or molecule that comprises at least one immunoglobulin variable domain with an exposed C-terminal region, in which said at least one immunoglobulin variable domain with an exposed C-terminal region is a VH domain, a VHH domain or an immunoglobulin variable domain that has been derived from a VH domain or VHH domain (such as the immunoglobulin variable domains mentioned herein).

As also further described herein, according to one particular aspect of the invention, the ADA assay described herein can be used to detect or measure ADA's in a suitable sample against a protein, polypeptide or other compound or molecule that comprises at least one immunoglobulin variable domain with an exposed C-terminal region, in which said at least one immunoglobulin variable domain with an exposed C-terminal region is an immunoglobulin single variable domain (as further described herein). More in particular, the ADA assay described herein can be used to detect or measure ADA's in a suitable sample against a protein, polypeptide or other compound or molecule that comprises at least one immunoglobulin variable domain with an exposed C-terminal region, in which said at least one immunoglobulin variable domain with an exposed C-terminal region is an immunoglobulin single variable domain that is a nanobody (as further defined herein; and in particular, a VHH domain, a humanized VHH domain or a camelized VH domain such as a camelized human VH domain) or another immunoglobulin single variable domain that is or has been derived from a VH domain such as a human VH domain (again as further described herein; and for example a VH-derived dAb™ or another VH-derived (single) domain antibody).

As also further described herein, the ADA assay of the invention can be applied to any suitable sample (as further described herein) which is to be tested for the presence of ADA's against a protein, polypeptide or other compound or molecule (as further described herein) and/or in which the amount, level or concentration of such ADA's is to be measured or determined. The ADA assay of the invention can in particular be applied to suitable samples (as further described herein) that have been obtained from a subject to which said protein, polypeptide or other compound or molecule (as further described herein) has been administered (again, as further described herein, for example as part of treatment of a subject or patient with said biologic or as part of a clinical trial involving administration of said biologic to a subject). For example, the sample may be a sample of whole blood, serum and plasma, ocular fluid, bronchoalveolar fluid/BALF, cerebrospinal fluid or another biological fluid; and will often be a blood sample, plasma sample or serum sample.

Although the invention is again not limited to any explanation, hypothesis or mechanism of action (so that generally, the term "true" ADA as used herein generally comprises any antibody or similar factor—other than any interfering factors—that is or can be present in a sample to be tested and that can specifically bind to the protein, polypeptide or other compound or molecule that has been administered to the subject from which the sample to be tested has been obtained), it will be clear to the skilled person that—in each case different from such interfering factors—such "true" ADA's will generally be antibodies; and that such "true" ADA's may be (and usually are) generated by the immune system of the subject or patient following (and in particular, as a response to and more in particular as an immune response to) the administration of and/or treatment with the administered protein, polypeptide or other compound or molecule (in particular where such administration or treatment is repeated such that the immune system is triggered to generate such ADA's).Such ADA's are also referred to herein and in the prior art as "treatment-emergent ADA's").

Thus, in a first aspect, the invention provides an assay, method or technique for measuring ADA's against (and in particular, specific for) a protein, polypeptide or other compound or molecule that comprises at least one immunoglobulin variable domain (and in particular, at least one VH-domain, VHH-domain or other domain that has been derived from a VH- or VHH-domain); which assay, technique or method is as further described herein (i.e. comprises steps a) to c) as further described herein).

In a further aspect, the invention provides an assay, method or technique for measuring ADA's against (and in particular, specific for) a protein, polypeptide or other compound or molecule that comprises at least one immunoglobulin variable domain (and in particular, at least one VH-domain, VHH-domain or other domain that has been derived from a VH- or VHH-domain) in a sample (as further described herein) that has been obtained from a subject or patient to which said protein, polypeptide or other compound or molecule has been administered; which assay, technique or method is as further described herein (i.e. comprises steps a) to c) as further described herein).

In a further aspect, the invention provides an assay, method or technique for measuring ADA's against (and in particular, specific for) a protein, polypeptide or other compound or molecule that comprises at least one immunoglobulin variable domain (and in particular, at least one VH-domain, VHH-domain or other domain that has been derived from a VH- or VHH-domain) that has an exposed (as defined herein) C-terminal region (or that may have and/or is suspected to have an exposed C-terminal region); which assay, technique or method is as further described herein (i.e. comprises steps a) to c) as further described herein).

In a further aspect, the invention provides an assay, method or technique for measuring ADA's against (and in particular, specific for) a protein, polypeptide or other compound or molecule that comprises at least one immunoglobulin variable domain (and in particular, at least one VH-domain, VHH-domain or other domain that has been derived from a VH- or VHH-domain) that has an exposed (as defined herein) C-terminal region (or that may have and/or is suspected to have an exposed C-terminal region) in a sample (as further described herein) that has been obtained from a subject or patient to which said protein, polypeptide or other compound or molecule has been administered; which assay, technique or method is as further described herein (i.e. comprises steps a) to c) as further described herein).

In the above aspects, the at least one immunoglobulin variable domain that is present in the protein, polypeptide or other compound or molecule (and that, in particular, may have an exposed C-terminal region) may in particular be a VH-domain, VHH-domain or other domain that has been derived from a VH- or VHH-domain. In one specific aspect, said at least one immunoglobulin variable domain is an immunoglobulin single variable domain (i.e. an immunoglobulin single variable domain that is capable for forming a (fully) functional antigen binding site without the VH/VL interaction that is required for the variable domains of conventional four-chain antibodies and in particular an ISV that is or has been derived from a VHH domain or a VH domain. Reference is for example made to WO09/138519 (or in the prior art cited in WO09/138519) and WO08/020079 (or in the prior art cited in WO08/020079). More in particular, such an ISV may be a VHH domain, a nanobody, a (single) domain antibody or a dAb (and in particular, a (single) domain antibody or dAb that is derived from a VH-domain, such as a human VH-domain).

Examples of proteins, polypeptides or other compounds or molecules that comprise at least one such ISV will be clear to the skilled person, again for example from WO09/138519 (or in the prior art cited in WO09/138519) or WO08/020079 (or in the prior art cited in WO 08/020079).

However, based on the disclosure herein and also from the disclosures by Nieba et al. and from WO11/07586 (both mentioned above), it will be clear to the skilled person that the present invention in its broadest sense is not limited to (assays, methods and techniques for measuring ADA's against) proteins, polypeptides or other compounds or molecules that comprise at least one such ISV (and in particular, at least one such ISV with an exposed C-terminal region), but can generally be applied to any protein, polypeptide or other compound or molecule that contains an immunoglobulin variable domain (and in particular VH-domain) that has an exposed C-terminal region. As illustrated by Nieba et al. and by WO11/07586, such a protein, polypeptide or other compound or molecule may for example also be an ScFv.

Generally, any such protein, polypeptide or other compound or molecule is said to comprise an immunoglobulin variable domain (as further defined herein) with an exposed C-terminal end/region when such protein, polypeptide or other compound or molecule undergoes a binding interaction at such a C-terminal end/region with one or more of the interfering factor(s) referred to herein and/or in the prior art cited herein (in particular, under physiological conditions and/or under the conditions commonly used in an ADA assay, such as the conditions used in the ADA assay that is described in the Experimental Part below); or that under such conditions is capable of undergoing such a binding interaction. Based on the disclosure herein and in the cited prior art, the skilled person will be able to determine whether a given protein, polypeptide or other compound or molecule has such an exposed C-terminal region (and/or is capable of undergoing such a binding interaction), for example by testing the relevant biologic against one or more samples that are known or suspected to contain such interfering factors.

Often/usually, such an exposed C-terminal region will be at the C-terminal end of the entire protein, polypeptide or other compound or molecule; however, the invention in its broadest sense is not limited thereto as it may also be that the exposed C-terminal region is somewhere else within the protein, polypeptide or other compound or molecule, provided that such C-terminal region is (still) accessible for such binding interaction, for example because it is not (or not sufficiently) covered or shielded by another domain (such as a further domain that is linked to the C-terminal end) in the protein, polypeptide or other compound or molecule. It may also be that the C-terminal end is linked to a linker (that in turn is linked to one or more further domains) that is so flexible that the C-terminal region is still accessible for binding by the interfering factor(s).

Overall, as is well known for immunoglobulin variable domains generally, the ISVD's invention will comprise 4 framework regions (FW1, FW2. FW3 and FW4) and 3 CDR's (CDR1, CDR2 and CDR3). As with immunoglobulin variable domains generally, the sequence of the CDR's will depend on the antigen/target(s) to which the ISVD has been raised and/or are intended to bind. The framework regions can generally be any suitable framework regions for ISVDs (optionally in association with one or more of the CDR's). For example, if the ISV is a Nanobody, the framework regions will generally contain a suitable number of VHH hallmark residues (e.g. at positions 11, 37, 44, 45, 47, 83, 84, 103, 104 and/or 108; see for example Tables A-3 and A-5 to A-8 of WO08/020079); one or more other amino acid residues that can be present in VHH's/Nanobodies (such as one or more humanizing substitutions that are known per se for VHH's and Nanobodies; reference is for example made to the teaching in WO08/020079) and/or one or more other suitable amino acid residues or substitutions for VHH's/Nanobodies; or any suitable combination of such amino acid residues/substitutions.

In addition, said ISVD or Nanobody (or a protein/polypeptide/compound comprising the same) can further contain one or more suitable amino acid residues, substitutions, deletions and/or additions that are known per se for such an ISVD or Nanobody, including without limitations one or more amino acid residues, substitutions, deletions and/or additions that reduce (or are intended to reduce) the binding of pre-existing antibodies to the ISVD/Nanobodies. These include the amino acid residues, substitutions, additions or deletions mentioned in the prior art cited herein, such as a C-terminal extension as described in WO12/175741 and/or one or more of the amino acid substitutions in or close to the C-terminal region as described in WO 12/175741, Harmsen et al. and Nieba et al. (such as for example at or close to positions 11, 14, 41, 83, 84, 89, 108 and/or the C-terminal VTVSS sequence) and/or in WO11/07586 or WO 13/024059.

As further set out herein, in addition to said at least one immunoglobulin variable domain with the exposed C-terminal end/region, the biologic may contain one or more other binding domains, binding units or (functional) moieties; in which the different domains, units or moieties that make up the biologic may be suitably linked to each other, such as via one or more suitable linkers.

In one aspect, as further set out herein, the biologic has a half-life (as defined herein) of at least 1 day, preferably at least 3 days, more preferably at least 7 days, such as at least 10 days, in a human subject. As also further set out herein, the biologic may for example comprise one or more binding domains, binding units or other functional groups or moieties that confer such a(n) (increased) half-life to the biologic.

As set out further herein, one specific but non-limiting example of such a binding domain that can be present in the biologic in order to confer such a(n) (increased) half-life to the biologic is an ISVD that is directed against a serum protein such as serum albumin (in particular, against human serum albumin). Thus, in one specific aspect of the invention, the biologic contains at least one such ISVD directed against a (human) serum protein (such as against human serum albumin). According to a more specific aspect of the invention, such ISVD against a serum protein is the ISVD with the exposed C-terminal end/region. For example, in one specific aspect of the invention, such ISVD against the serum protein is present at and/or forms the C-terminal end of the biologic. Some non-limiting examples of such ISVD's against human serum albumin can be found in WO06/122787 and WO12/175400, and for example include the serum-albumin binding Nanobody called "Alb-1" in WO06/122787 and its humanized variants (such as the serum-albumin binding Nanobody called "Alb-8" in WO06/122787 and the serum-albumin binding Nanobody called "Alb-23" in WO12/175400).

Also, in a preferred but non-limiting aspect, the biologics referred to herein are preferably suitable and/or intended for administration to a human subject (in particular, as a therapeutic, prophylactic, diagnostic or drug); or are suitable and/or intended for use in an animal model (such as a disease model).

In the present specification, whenever the term "ISV" is used, it should be understood that:

such an ISV is preferably a Nanobody, in which the term "Nanobody" is generally as defined in or WO08/020079 or WO09/138519, and thus in a specific aspect generally denotes a VHH, a humanized VHH or a camelized VH (such as a camelized human VH) or generally a sequence optimized VHH (such as e.g. optimized for chemical stability and/or solubility, maximum overlap with known human framework regions and maximum expression). It is noted that the terms Nanobody or Nanobodies are registered trademarks of Ablynx N.V. and thus may also be referred to as Nanobody® and/or Nanobodies®);

the term "ISV" in its broadest sense also includes "ISV-based biologicals" and, when the ISV is a Nanobody, "Nanobody-based biologicals". An "ISV-based biological" is defined herein as a protein, polypeptide or other biological drug that comprises or essentially consists of at least one (such as one, two or three) ISV's. Similarly, a "Nanobody-based biological" is defined as a protein, polypeptide or other biological drug that comprises or essentially consist of at least one (such as one, two or three) Nanobodies. As with the term "ISV", whenever the term "ISV-based biological" is used, it should be understood that such an ISV-based biological is preferably a Nanobody-based biological. Within the context of the present invention, both an "ISV-based biological" and a "Nanobody-based biological" may for example be a monovalent, bivalent (or multivalent), bispecific (or multispecific), and biparatopic (or "multiparatopic) ISV construct or Nanobody construct, respectively. Also, any ISV-based or Nanobody-based biological may for example, in addition to the one or more (such as one, two or three) ISV's or Nanobodies, optionally further comprise one or more (such as one or two) other further therapeutic moieties and/or one or more (such as one or two) other moieties that influence the pharmacokinetic or pharmacodynamic properties of the ISV-based or Nanobody-based biological (such as its half-life). Suitable examples of such further therapeutic or other moieties will be clear to the skilled person, and for example generally can include any therapeutically active protein, polypeptide or other binding domain or binding unit, as well as for example modifications such as those described on pages 149 to 152 of WO09/138159. An ISV-based biological or Nanobody-based biological is preferably a therapeutic or intended for use as a therapeutic (which includes prophylaxis and diagnosis) and for this purpose preferably contains at least one ISV against a therapeutically relevant target (such as for example RANK-L, vWF, IgE, RSV, CXCR4, IL-23 or other interleukins, etc.). For some specific but non-limiting examples of such ISV-based or Nanobody-based biologicals, reference is for example made to the various applications by Ablynx N.V. (such as for example and without limitation WO2004/062551, WO2006/122825, WO 2008/020079 and WO2009/068627), as well as for example (and without limitation) to applications such as WO06/038027, WO06/059108, WO07/063308, WO07/063311, WO 07/066016 and WO07/085814. These references also give examples of different nanobody formats (such as bispecific and biparatopic constructs) and suitable linkers that can be used to make such constructs. Also, as further described herein, an ISVD or Nanobody as described herein may be directed against a (human) serum protein such as (human) serum albumin, and such an ISVD or Nanobody may also find therapeutic uses, in particular in and/or for extending the half-life of therapeutic moieties and compounds (such as in or for the ISV-based biologicals described herein). Reference is for example made to WO2004/041865, WO2006/122787 and WO2012/175400, which generally describe the use of serum-albumin binding nanobodies for half-life extension. Also, in the present specification, unless explicitly mentioned otherwise herein, all terms mentioned herein have the meaning given in WO 09/138519 (or in the prior art cited in WO09/138519) or WO08/020079 (or in the prior art cited in WO08/020079). Also, where a method or technique is not specifically described herein, it can be performed as described in WO09/138519 (or in the prior art cited in WO 09/138519) or WO08/020079 (or in the prior art cited in WO08/020079).

Also, the following terms have the same meaning as given on, and/or where applicable can be determined in the manner described in, pages 62-75 of WO09/138519: "agonist", "antagonist", "inverse agonist", "non-polar, uncharged amino acid residue", "polar uncharged amino acid residue", "polar, charged amino acid residue", "sequence identity", "exactly the same" and "amino acid difference" (when referring to a sequence comparison of two amino acid sequences), "(in) essentially isolated (form)", "domain", "binding domain", "antigenic determinant", "epitope", "against" or "directed against" (an antigen),"specificity" and "half-life". In addition, the terms "modulating" and "to modulate", "interaction site", "specific for", "cross-block", "cross-blocked" and "cross-blocking" and "essentially independent of the pH" are as defined on (and/or can be determined as described on) pages 74-79 of WO10/130832 of applicant. Also, when referring to a construct, compound, protein or polypeptide of the invention, terms like "monovalent", "bivalent" (or "multivalent"), "bispecific" (or "multispecific"), and "biparatopic" (or "multiparatopic") may have the meaning given in WO 09/138.519, WO10/130832 or WO08/020079.

The term "half-life" as used herein relation to a protein, polypeptide or other compound or molecule (and in particular, an ISV, Nanobody, ISV-based biological, Nanobody-based biological or any other amino acid sequence, compound or polypeptide can generally be defined as described in paragraph o) page 57 of WO08/020079 and as mentioned therein refers to the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally be as described in paragraph o) on page 57 of WO08/020079. As also mentioned in paragraph o) on page 57 of WO08/020079, the half-life can be expressed using parameters such as the t1/2-alpha, t1/2-beta and the area under the curve (AUC). In this respect it should be noted that the term "half-life" as used herein in particular refers to the t1/2-beta or terminal half-life (in which the t1/2-alpha and/or the AUC or both may be kept out of considerations). Reference is for example made to the Experimental Part below, as well as to the standard handbooks, such as Kenneth, A et al: Chemical Stability of Pharmaceuticals: A Handbook for Pharmacists and Peters et al, Pharmacokinete analysis: A Practical Approach (1996). Reference is also made to "Pharmacokinetics", M Gibaldi & D Perron, published by Marcel Dekker, 2nd Rev. edition (1982). Similarly, the terms "increase in half-life" or "increased half-life" as also as defined in paragraph o) on page 57 of WO08/020079 and in particular refer to an increase in the t1/2-beta, either with or without an increase in the t1/2-alpha and/or the AUC or both.

When a term is not specifically defined herein, it has its usual meaning in the art, which will be clear to the skilled person. Reference is for example made to the standard handbooks, such as Sambrook et al, "Molecular Cloning: A Laboratory Manual" (2nd.Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985) Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, UK (2001); and Janeway et al., "Immunobiology" (6th Ed.), Garland Science Publishing/Churchill Livingstone, New York (2005), as well as to the general background art cited herein.

Also, herein, the amino acid residues of a Nanobody are numbered according to the general numbering for VH domains given by Kabat et al. ("Sequence of proteins of immunological interest", US Public Health Services, NIH Bethesda, Md., Publication No. 91), as applied to VHH domains from Camelids in the article of Riechmann and Muyldermans, J. Immunol. Methods 2000 Jun. 23; 240 (1-2): 185-195; or referred to herein. According to this numbering, FR1 of a Nanobody comprises the amino acid residues at positions 1-30, CDR1 of a Nanobody comprises the amino acid residues at positions 31-35, FR2 of a Nanobody comprises the amino acids at positions 36-49, CDR2 of a Nanobody comprises the amino acid residues at positions 50-65, FR3 of a Nanobody comprises the amino acid residues at positions 66-94, CDR3 of a Nanobody comprises the amino acid residues at positions 95-102, and FR4 of a Nanobody comprises the amino acid residues at positions 103-113. [In this respect, it should be noted that—as is well known in the art for VH domains and for VHH domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa].

Alternative methods for numbering the amino acid residues of VH domains, which methods can also be applied in an analogous manner to VHH domains from Camelids and to Nanobodies, are the method described by Chothia et al. (Nature 342, 877-883 (1989)), the so-called "AbM definition" and the so-called "contact definition". However, in the present description, aspects and figures, the numbering according to Kabat as applied to VHH domains by Riechmann and Muyldermans will be followed, unless indicated otherwise.

It should also be noted that the Figures, any Sequence Listing and the Experimental Part/Examples are only given to further illustrate the invention and should not be interpreted or construed as limiting the scope of the invention and/or of the appended claims in any way, unless explicitly indicated otherwise herein.

As mentioned herein, the ADA assays of the invention are adaptations of known bridging assay formats known per se from the prior art.

Generally, such ADA assays for determining anti-drug antibodies against a given biological drug or compound are standard knowledge in the field of pharmacology and they are routinely used during the clinical development of biological drug products (as well as being required by various regulatory agencies around the world). In addition, it is envisaged that ADA assays can be used to monitor occurrence of treatment emergent antibodies in patients treated with a given drug and based on the results treatment can be amended or changed, therefore, such ADA assays may be important diagnostic means to guide physicians in designing optimal treatment for patients. Reference is for example made to the reviews by Wadhwa and Thorpe, Bioanalysis (2010), 2(6), 1073-1084 and by Shankar et al., Journal of Pharmaceutical and Biomedical Analysis, 48 (2008), 1267-1281; as well as Wadwha and Thorpe, Journal of Immunotoxicology, 3:115-121, 2006; Mire-Sluis et al., J. Immunol. Meth. 289 (2004), 1-16; Peng et al., Journal of Pharmaceutical and Biomedical Analysis, 54, (2011), 629-635; and Loyet et al., J. Immunol. Meth. 345 (2009), 17-28.

It is also known that there are different assays, methods and techniques for performing ADA assays, including (i) ELISA—Bridging Format; (ii) ELISA—Direct Format; (iii) Indirect Format; (iv) Radio Immuno-precipitation Assay (RIP); (v) Surface Plasmon Resonance; and (vi) Electrochemiluminescence-Bridging Format (also referred to in the art as an "ECL-assay" or "ECL-format"). Reference is for example made to Table 1 in the aforementioned review by Mire-Sluis et al., Table 1 in the 2010 review by Wadwha and Thorpe, and Table 2 in the 2006 article by Wadwha and Thorpe.

As mentioned in the 2010 review by Wadwha and Thorpe (see pages 1079-1080 and FIG. 2), one platform that is currently often used in performing ECL assays is the "Meso Scale Discovery" or "MSD platform", available from Meso Scale Diagnostic LLC. This is abridging assay format that uses ruthenium labels that emit light when electrochemically stimulated for detection.

FIG. 1 schematically shows the principles of prior art bridging assay formats (such as ELISA-bridging format or ECL bridging format) for detecting ADA's (indicated as (1) in FIG. 1) against a conventional antibody (indicated as (2) in FIG. 1). In this format, the sample to be tested for the presence of the ADA's (1) is contacted with the conventional antibody (2) (also referred to as the "capture agent") that is immobilized on a solid support (4) using a suitable covalent or usually non-covalent binder or linker (3) (such as a biotin-steptavidin pair), under conditions that are such that any ADA's (1) in the sample can bind to/are captured by the capturing agent (2).

After any ADA's (1) in the sample have been allowed to bind to the immobilized conventional antibody (2), the non-bound constituents of the sample are washed away using one or more suitable washing steps. The support with the conventional antibody (2) and any ADA's (1) bound to it is then contacted with a "detection agent" (which in the case of the assay shown in FIG. 1 is a second conventional antibody (5) which is either linked directly or via a suitable linker (7) to a detectable label or tag (6) such as, in the case of an ECL assay, a ruthenium label such as SULFO-TAG™ or MSD TAG or another suitable label that can be detected using electrochemoluminescense techniques), under conditions such that the detection agent can bind to the complex of the conventional antibody (2) and the ADA (1).

Usually, in an assay of the format described in FIG. 1, the detection agent used is a suitably tagged or labeled version of the conventional antibody (2), so that the conventional antibodies (2) and (5) in FIG. 1 are the same, with one being immobilized on the support and used as the "capture agent" and the other being suitably tagged or labeled and used as the "detection agent". After the detection agent has been allowed to bind to the complex of the capturing agent (2) and the ADA (1), any excess detection agent is then washed away (i.e. by means of one or more suitable washing steps), after which the presence of detection agent remaining on the solid support (i.e. as part of the complex comprising the capture agent (2), the ADA (1) and the detection agent (3)) is determined or measured using the detectable label or tag (such as, in the case of an ECL assay, by means of electrochemiluminescence). The amount or level of detectable label or tag remaining is then a measure for the amount of ADA's in the sample.

Methodologies and techniques for performing the above ADA assays (such as assay conditions, assay buffers, washing steps, solid supports and linkers for immobilizing the capturing agent and methods for doing the same, suitable tags/labels and methods for linking them to the detection agent, techniques for detecting/measuring the detectable label, and equipment for performing the assays) are known per se (for example from the prior art cited herein or from manufacturer's instructions) or commercially available.

However, as indicated in WO2012/175741, when such a known ADA assay format is used for detecting or measuring ADA's against polypeptides, proteins or other biological compounds that comprise an immunoglobulin variable domain with an exposed C-terminus, interfering factors present in the sample tested may interfere with (the reliability of) said assay and prevent a proper read-out (i.e. reflective of the amount of "true" ADA's in the sample) to be obtained.

For this reason, in their work leading up to the present invention, the present inventors have tested different ADA assay formats to see which of these formats are susceptible to protein interference and whether such existing assay formats can be adapted or modified to provide an assay, method or technique that can be used to determine/measure ADA's (and in particular treatment-emergent ADA's) in samples that contain (or are suspected to contain) interfering factors.

In particular, as described in the Experimental Part, the inventors have tested five different ADA assay formats (a homogeneous ECL based bridging format known per se; a sequential ECL based bridging format known per se; a sequential ELISA based bridging format known per se; a direct ELISA format known per se; and homogeneous ECL based bridging format that has been modified in accordance with the present invention); and in doing on have found that of these different assay formats, a (homogeneous) ECL bridging assay can be adapted as set out herein (i.e. through the use of a detection agent or a capture agent that has been modified as set out herein) to provide an ADA assay format that can be used to measure ADA's (and in particular treatment-emergent ADA's) against a biologic even in a sample that contains (or is suspected to contain) interfering proteins. It is (in part) on the basis of these results and findings that the present invention is based.

Generally, in their research leading up to the invention, the inventors have found that a known bridging assay format for measuring ADA's against a biologic (and in particular a biologic that contains at least one immunoglobulin variable domain with an exposed C-terminal region) can be modified and improved (i.e. so as to allow the detection of "true" ADA's and in particular treatment emergent ADA's, even in samples that contain or are expected/suspected to contain interfering factors) by using, as either the capturing agent or as the detection agent, the biologic which has 1-10 (and preferably 1-5) amino acid residues added to the exposed C-terminal end (in particular where said exposed C-terminal end forms the C-terminal end of the entire biologic). The 1-5 added amino acid residues added to the C-terminal end can be any suitable amino acid residues, and can for example be as described in WO12/175741. For example, it has already been found that using, as the capturing agent or the detection agent, the biologic with one C-terminal alanine residue added already provides a major improvement in assay performance (see the further data presented in the Experimental Part).

One way of performing the assay according to the invention is schematically shown in FIGS. 2A to 2D (using a bivalent ISV construct as an example) and FIG. 3 (using a monovalent ISV as an example). As can be seen from these Figures (and also FIG. 4 discussed further herein), the assay according to the invention is based on the general principles of known ADA bridging assays (with some novel modifications as described herein) and advantageously can be performed using known methodologies and equipment for performing prior art bridging format ADA assays (again, with the adaptations mentioned herein).

As described herein, the ADA assay of the invention can be used to detect ADA's (1) against an ISV or ISV-construct (and in particular, an ISV or ISV construct that has or is expected to have an exposed C-terminal end/region as further described herein).

In FIGS. 2A to 2D, by means of non-limiting example, the assay of the invention is illustrated by the use of the assay in detecting ADA's (1) against a bivalent ISV construct (8) that comprises a first ISV (8a) and a second ISV (8b) that are linked via a suitable linker (8c), in which the first ISV (8a) and the second ISV (8b) can be the same or different (in the latter case, the bivalent ISV construct is bispecific or, in case the ISV's are directed against different epitopes on the same target, biparatopic). However, it should be understood that the assay of the invention can also be used for measuring ADA's against a monovalent ISV (see FIG. 3) or a tri- or multivalent ISV (not shown).

It should also be understood that in the paragraphs below, the assays of the invention are described in the so-called "sequential set-up", in which the steps of contacting the sample containing the anti-drug antibodies with the capturing agent (also referred to herein as "step a)") and contacting the captured anti-drug antibodies with the detection agent (also referred to herein as "step c)") are carried out sequentially (i.e. one after the other) and are usually separated by a washing step (also referred to herein as "step b)"). However, it will be clear to the skilled person that other set-ups or variations of the set-up described herein will also be possible. One such set-up/variation which is important in the practice of the invention is the so-called "homogeneous" set-up in which steps a) and c) are carried out essentially simultaneously, i.e. by adding the sample and the detection agent essentially at the same time (i.e. directly/shortly after one another) to the support with the capturing agent and without the intermediate washing step b), or by first mixing/contacting the sample with the detection agent and then contacting/applying it with/to the support with the capturing agent. It should also be noted that the assays used in Examples 1 and 2 below are examples of assays in the homogeneous format.

In the assay of the invention (sequential set-up), the bivalent ISV construct (8) is used as the "capture agent" and for this purpose is immobilized on the solid support (4) using a suitable binder or linker (3), such as an avidin-steptavidin binding pair or another suitable non-covalent binding pair. The sample to be tested is then contacted with the immobilized bivalent ISV construct (8) (i.e. under conditions such that any ADA's (1) present in said sample can bind to/are captured by the capturing agent (8)) and any ADA's (1) against the bivalent ISV construct (8) are allowed to bind to the construct/capture agent, after which the non-bound proteins and other constituents of the sample are removed by one or more suitable washing steps (performed in a manner known per se). The solid support (4) with the complex of the capture agent (8) and the ADA's (1) then contacted with the detection agent (9) that is labeled or tagged, either directly or via a suitable linker (7), with a detectable label or tag (again, for the ECL format, a tag or label known per se for performing ECL assays can be used, such as SULFO-TAG™, MSD TAG or another suitable (ruthenium-based) electrochemiluminescense label); under conditions such that the detection agent (9) can bind to the complex of the capturing agent (8) and the ADA (1). The detection agent (9) is then allowed to bind to the complex of the capturing agent (8) and the ADA (1), after which any excess detection agent is then removed (i.e. using one or more suitable washing steps known per se) and the remaining complex formed by the capturing agent (8), the ADA (1) and the detection agent (9) is detected and/or the amount thereof measured) by means of detecting the presence of/measuring the amount of detectable tag or label in a manner known per se (i.e., in the case of an assay in the ECL format, using suitable electrochemiluminescence techniques).

In the assay of the invention, the detection agent (9) will usually be the same (or essentially the same) as the bivalent ISV construct (5), albeit that: (a) the detection agent (9) is not linked to the solid support; (b) the detection agent (9) is tagged or labeled with the detectable tag or label (6), optionally via a suitable linker (7); and (c) where the bivalent ISV construct (8) has an exposed C-terminal region, the detection agent (9) has, compared to the capturing agent (8), 1-5 amino acid residues (indicated as (8d) in FIG. 2C) added to its C-terminal end (essentially as described in WO13/024059 and in particular in WO12/175741 mentioned above).

As can be seen from the data shown in the Experimental Part, according to the invention, it has surprisingly been found that when a detection agent (9) is used that is the same as the ISV construct (8) but that has such 1-5 amino acid residues added to its C-terminal end, that the assay can be used to measure or determine "true" ADA's even in the presence of interfering factors in the sample. By contrast, when a detection agent (9) is used that is the same as the capturing agent (8) and that does not have such 1-5 further amino acid residues added to its C-terminal end, then the interfering factor(s) may interfere with the assay and make it more difficult or even impossible to measure (only) the true ADA's (1) against the bivalent ISV construct (8).

Similarly, FIG. 3 schematically shows the use of the assay of the invention in measuring ADA's (1) against a monovalent ISV (10). Again, the monovalent ISV (10) is used as the capturing agent and for this purpose is suitably immobilized via linker (3) to support (4). The immobilized monovalent ISV (10) is again contacted with the sample (i.e. under conditions such that allow any ADA's (1) present in said sample to bind to/be captured by the capturing agent (10)) and any ADA's (1) present in the sample are allowed to bind to the capturing agent (10). The other constituents of the sample as removed by means of one or more suitable washing steps.

The ADA's (1) captured by the monovalent ISV (10) are then detected using a detection agent (11), which is the same as the monovalent ISV (10), albeit that: (a) the detection agent (11) is not linked to the solid support; (b) the detection agent (11) is tagged or labeled with the detectable tag or label (6), optionally via a suitable linker (7); and (c) the detection agent (11) has, compared to the capturing agent (10), 1 to 5 amino acid residues (indicated as (12) in FIG. 3) added to its C-terminal end (essentially as described in WO13/024059 and in particular in WO12/175741 mentioned above). Again, for this purpose, the complex of the capturing agent (10) and the ADA (1) is contacted with the detection agent (11) under conditions such that allow the detection agent (11) to bind to the complex of the capturing agent (10) and the ADA (1). In the sequential set-up, the excess detection agent is then removed (i.e. using one or more suitable washing steps known per se), after which the detectable tag/label remaining is detected/measured in a manner known per se. In the homogeneous set-up a mixture of serum components and labeled detector and capture agent is allowed to equilibrate such that complexes of antibodies (or other matrix components) with the labeled agents are formed. The mixture containing pre-formed complexes is added to capturing plates where complexes are bound close to the plates and an ECL read out permits detection of a electroluminescence current rendering multiple washing steps superfluous. Non-captured components of the sample will not render a meaningful detection signal).

An alternative way of performing the assays of the invention is schematically shown in FIGS. 4A to 4C (using a bivalent ISV construct as an example). The assay of FIGS. 4A to 4C is performed in essentially the same manner as the assays shown in FIGS. 2A to 2D and in FIG. 3; however, in this embodiment of the assays of the invention, instead of the detection agent (9) having 1 to 10 (and preferably 1-5) amino acid residues added at its C-terminal end, said 1 to 10 amino acid residues (8d in FIG. 4B) have been added to the C-terminal end of the capturing agent (8). Thus, as can be seen from FIGS. 4B and 4C, the capturing agent (8) comprises a first and a second ISV ((8a) and (8b) in FIG. 4A, respectively), of which the first ISV (8a) is linked to the solid support (4) by means of the linker (3), of which and the second ISV (8b) (which is suitably linked to the first ISV (8a) by means of linker (8c)) has 1 to 10 amino acid residues at its C-terminal end (indicated as (8d) in FIG. 4B), essentially as described in WO2013/024059 and in particular in WO2012/175741 mentioned above. The detection agent (9) can again be essentially the same as the capturing agent (8), albeit that (a) the detection agent (9) is not linked to the solid support (4); (b) the detection agent (9) is tagged or labeled with the detectable tag or label (6), optionally via a suitable linker (7); and (c) compared to the capturing agent (8), the detection agent (9) does not have 1-5 amino acid residues (indicated as (8d) in FIG. 2C) added to its C-terminal end (in other words, the detection agent instead of the capturing agent has an exposed C-terminal end, e.g. ending with the C-terminal amino acid residues VTVSS).

The assay shown in FIGS. 4A to 4C can essentially be performed in the same way as the assays shown in FIGS. 2A to 2D and in FIG. 3. The sample to be tested is contacted with the carrier/support (4) on which the detection agent (8) is immobilized (i.e. via the linker (3), which may for example be an avidin-streptavidin binding pair), under conditions such that any ADA's (1) in the sample can bind to/be captured by the capturing agent (8). In the sequential set-up, after the ADA's (I) have been allowed to bind to the capturing agent (8), the further constituents of the sample are removed by one or more suitable washing steps (in the homogeneous set-up, as described in more detail herein, the tag/label is measured after the support with the capturing agent, the sample and the detection agent have been contacted with each other. Non-captured components of the sample will not render a meaningful detection signal). After that, the complex of the ADA's (1) and the capturing agent (8) immobilized on the solid support (4) is contacted with the detection agent (9) under conditions such that the detection agent (9) can bind to said complex. After the detection agent (9) has been allowed to bind to said complex, excess detection agent (9) is removed by washing after which the presence or amount, respectively, of the detectable tag or label (7) bound to the complex is detected or measured, respectively, again using a suitable manner known per se (such as, where the detectable tag or label (7) is a tag or label that can be detected or measured using electrochemiluminescense techniques, a suitable electrochemiluminescense technique).

With respect to FIGS. 2A, 2B, 3, 4A and 4B, it should be noted that, when the capturing agent is linked to the solid support via an avidin-strepavidin binding pair (which is one preferred way of linking the capturing agent to the solid support), the capturing agent may be linked to the support via one or more linkers (3), depending on the number of biotin residues that are linked to the capturing agent (usually via lysine residues that are present in the capturing agent). For example, as schematically shown in FIG. 2D for the situation where the capturing agent is a bivalent nanobody construct, each of the nanobodies in the construct may be linked to the support via one or more avidin-streptavidin linkers (3), again depending on the number of biotins linked to each nanobody (in case of the bivalent construct shown as a non-limiting example in FIG. 2D, the nanobody (8a) is linked to the support via one avidin-streptavidin linker (3) and the nanobody (8b) is linked to the support via two avidin-streptavidin linkers (3)). Advantageously, the above steps can be performed using methodologies and techniques known per se for performing ECL-assays (such as assay conditions, assay buffers, washing steps, solid supports and linkers for immobilizing the capturing agent and methods for doing the same, suitable tags/labels and methods for linking them to the detection agent, techniques for detecting/measuring the detectable label, and equipment for performing the assays all known per se for performing ECL assays) or with only minor modifications of such known methodologies or techniques (which can be easily determined and applied by the person skilled in the art of ADA assays, optionally after a limited degree of trial and error). For example and without limitation, as with the known ECL assays described in FIG. 1, the assays of the invention can be performed using the Meso Scale Discovery platform, commercially available from Meso Scale Discovery LLC (see mesoscale.com). Other techniques include for example ELISA-based techniques and Delfia® immunoassays (the latter is also well suited for use in a homogeneous set-up as described herein).

Further, after the amount of label (i.e. corresponding to the amount of complex formed) has been measured/detected, (the different components corresponding to) the different signals may be further characterized, and/or the results/read-out obtained may be compared to the results obtained from other assays or measurements performed on the sample(s) (or on other samples, for example obtained from the same subject or group of subjects). In one aspect, the invention relates to a method for detecting and/or measuring anti-drug antibodies (such as, in particular but without limitation, treatment-emergent ADA's) against a protein, polypeptide or other compound or molecule (such as, in particular but without limitation, a biological compound) that comprises at least one immunoglobulin variable domain with an exposed C-terminal region (and in particular, at least one ISV with an exposed C-terminal region) in a sample, said method comprising at least the steps of:

a) contacting said sample with a capturing agent that is immobilized on a support, wherein said capturing agent is or essentially consists of said protein, polypeptide or other compound or molecule, under conditions such that any anti-drug antibodies against said protein, polypeptide or other compound or molecule can bind to said capturing agent;

b) (optionally) removing any components or constituents present in said sample that do not bind to the capturing agent;

c) detecting or measuring any anti-drug antibodies that have bound to the capturing agent, by contacting the complex of the capturing agent and any captured anti-drug antibodies with a detection agent, under conditions such that said detection agent can bind to (the complex of the capturing agent and) any captured anti-drug antibodies, wherein either:

x) said capturing agent is or essentially consists of: (i) said protein, polypeptide or other compound or molecule (immobilized on the solid support); and (ii) 1-5 amino acid residues that are linked to the exposed C-terminal end of the immunoglobulin variable domain with the exposed C-terminal region that is comprised within the protein, polypeptide or other compound or molecule;

or:

y) said detection agent is or essentially consists of: (i) said protein, polypeptide or other compound or molecule; (ii) a detectable tag or label bound to said protein, polypeptide or other compound or molecule (either directly or via a suitable linker) and (iii) 1-5 amino acid residues that are linked to the exposed C-terminal end of the immunoglobulin variable domain with the exposed C-terminal region that is comprised within the protein, polypeptide or other compound or molecule.

As indicated herein, in the sequential set-up of the methods of the invention, the above steps a) to c) will be carried out sequentially (and will usually include the washing step b); whereas in the homogenous set-up, steps a) and c) will be carried out essentially simultaneously (as described herein) and without the washing step b).

In another aspect, the invention relates to a method for detecting and/or measuring anti-drug antibodies (such as, in particular but without)imitation, treatment-emergent ADA's) against a protein, polypeptide or other compound or molecule (such as, in particular but without limitation, a biological compound) that comprises at least one immunoglobulin variable domain with an exposed C-terminal region (and in particular, at least one ISV with an exposed C-terminal region) in a sample, said method comprising at least the steps of:
a) contacting said sample with a capturing agent that is immobilized on a support, wherein said capturing agent is or essentially consists of said protein, polypeptide or other compound or molecule, under conditions such that any anti-drug antibodies against said protein, polypeptide or other compound or molecule can bind to said capturing agent;
b) (optionally) removing any components or constituents present in said sample that do not bind to the capturing agent;
c) detecting or measuring any anti-drug antibodies that have bound to the capturing agent, by contacting the complex of the capturing agent and any captured anti-drug antibodies with a detection agent, under conditions such that said detection agent can bind to (the complex of the capturing agent and) any captured anti-drug antibodies, wherein said capturing agent is or essentially consists of: (i) said protein, polypeptide or other compound or molecule (immobilized on the solid support); and (ii) 1-5 amino acid residues that are linked to the exposed C-terminal end of the immunoglobulin variable domain with the exposed C-terminal region that is comprised the protein, polypeptide or other compound or molecule.

Again, in the sequential set-up of the methods of the invention, the above steps a) to c) will be carried out sequentially (and will usually include the washing step b); whereas in the homogenous set-up, steps a) and c) will be carried out essentially simultaneously (as described herein) and without the washing step b).

In another aspect, the invention relates to a method for detecting and/or measuring anti-drug antibodies (such as, in particular but without limitation, treatment-emergent ADA's) against a protein, polypeptide or other compound or molecule (such as, in particular but without limitation, a biological compound) that comprises at least one immunoglobulin variable domain with an exposed C-terminal region (and in particular, at least one 1SV with an exposed C-terminal region) in a sample, said method comprising at least the steps of:
a) contacting said sample with a capturing agent that is immobilized on a support, wherein said capturing agent is or essentially consists of said protein, polypeptide or other compound or molecule, under conditions such that any anti-drug antibodies against said protein, polypeptide or other compound or molecule can bind to said capturing agent;
b) (optionally) removing any components or constituents present in said sample that do not bind to the capturing agent;
c) detecting or measuring any anti-drug antibodies that have bound to the capturing agent, by contacting the complex of the capturing agent and any captured anti-drug antibodies with a detection agent, under conditions such that said detection agent can bind to (the complex of the capturing agent and) any captured anti-drug antibodies, wherein said detection agent is or essentially consists of: (i) said protein, polypeptide or other compound or molecule; (ii) a detectable tag or label bound to said protein, polypeptide or other compound or molecule (either directly or via a suitable linker) and (iii) 1-5 amino acid residues that are linked to the exposed C-terminal end of the immunoglobulin variable domain with the exposed C-terminal region that is comprised within the protein, polypeptide or other compound or molecule.

Again, in the sequential set-up of the methods of the invention, the above steps a) to c) will be carried out sequentially (and will usually include the washing step b); whereas in the homogenous set-up, steps a) and c) will be carried out essentially simultaneously (as described herein) and without the washing step b).

The invention in particular related to a method as described herein in which the sample is a sample of whole blood, serum, plasma, lymph fluid, ocular fluid, bronchoalveolar fluid/BALF, cerebrospinal fluid or another biological fluid (such as sputum or nasal washes); and in particular a sample of whole blood, serum or plasma. Said sample may also be/have been suitably prepared for use in the assay of the invention (for example, by suitable dilution or extraction methods if appropriate).

The invention also relates to a method as further described herein, in which the sample has been obtained from a subject to which said protein, polypeptide or other compound or molecule has been administered and wherein (i) the protein, polypeptide or other compound or molecule has a half-life that is such there is a risk or possibility that anti-drug antibodies against protein, polypeptide or other compound or molecule have been raised in the subject to which said protein, polypeptide or other compound or molecule has been administered (for example, such a protein, polypeptide or other compound or molecule may have a half-life that is as further indicated herein); and/or (i) the protein, polypeptide or other compound or molecule has been administered to a subject according to a regimen that is such that there is a risk or possibility that anti-drug antibodies against protein, polypeptide or other compound or molecule have been raised in the subject to which said protein, polypeptide or other compound or molecule has been administered (for example, wherein the protein, polypeptide or other compound or molecule has been administered repeatedly at relevant intervals, as will be clear to the skilled person/treating physician).

Where said protein, polypeptide or other compound or molecule is a drug or therapeutic, the sample may for example have been obtained from a patient that has been treated with said protein, polypeptide or other compound or molecule. Alternatively, the sample may for example have been obtained from a subject to which said biologic has been administered in the course of a clinical trial.

In another aspect, the invention relates to a method as further described herein, in which the at least one immunoglobulin variable domain with the exposed C-terminal end/region that is comprised within the biologic is a VH domain or has been derived from a VH domain. Again, such immunoglobulin variable domain is preferably an ISV and more in particular an ISV that is a VH domain, a VHH domain or an ISV that has been derived from a VH domain or a VHH domain.

In particular, the at least one immunoglobulin variable domain with the exposed C-terminal end/region may have the C-terminal amino acid sequence VTVSS (meaning that the last 5 C-terminal amino acid residues of the immunoglobulin variable domain with the exposed C-terminal end/region are VTVSS, as is usually the case for VH- and VHH-domains).

More in particular, the invention relates to a method as further described herein, in which the at least one immunoglobulin variable domain with the exposed C-terminal region comprised within said protein, polypeptide or other compound or molecule is a nanobody (such as, in particular, a VHH domain, a humanized VHH domain or a camelized VH domain such as a camelized human VH domain), a dAb or a (single) domain antibody; and preferably a nanobody.

However, it should be understood that the invention in its broadest sense is not limited to proteins, polypeptides or other compounds or molecules that comprise and/or are based on ISV's, but also comprises other biologics that may comprise one or more immunoglobulin variable domains with an exposed C-terminal region, such as ScFv fragments or diabodies.

The invention further relates to a method as further described herein, in which the at least one) immunoglobulin variable domain with the exposed C-terminal region (and in particular, the at least one ISV with the exposed C-terminal region) is present at (i.e. forms) the C-terminal region of said protein, polypeptide or other compound or molecule. In particular, where said at least one immunoglobulin variable domain has the C-terminal amino acid sequence VTVSS, said protein, polypeptide or other compound or molecule may also have the C-terminal amino acid sequence VTVSS (meaning that the last 5 C-terminal amino acid residues of the biologic are VTVSS).

The invention further relates to a method as further described herein, in which said protein, polypeptide or other compound or molecule is or essentially consists of a monovalent immunoglobulin single variable domain, The invention further relates to a method as further described herein, in which said protein, polypeptide or other compound or molecule comprises at least one immunoglobulin single variable domains and at least one other therapeutic moiety or entity (either linked directly or via a suitable linker).

The invention further relates to a method as further described herein, in which said protein, polypeptide or other compound or molecule comprises at least two (such as two, three, four or five) immunoglobulin single variable domains (either linked directly or via a suitable linker).

The invention further relates to a method as further described herein, in which said protein, polypeptide or other compound or molecule comprises at least two immunoglobulin single variable domains (either linked directly or via a suitable linker) that are the same.

The invention further relates to a method as further described herein, in which said protein, polypeptide or other compound or molecule comprises or essentially consists of at least two (such as two, three, four or five) immunoglobulin single variable domains (either linked directly or via a suitable linker) that are different.

The invention further relates to a method as further described herein, in which said protein, polypeptide or other compound or molecule comprises or essentially consists of at least two (such as two, three, four or five) immunoglobulin single variable domains (either linked directly or via a suitable linker) that are each directed to a different target (i.e. such that the resulting protein, polypeptide or other compound or molecule is a bi- or multispecific construct).

The invention further relates to a method as further described herein, in which said protein, polypeptide or other compound or molecule comprises or essentially consists of at least two (such as two, three, four or five) immunoglobulin single variable domains (either linked directly or via a suitable linker) that are each directed to different epitopes on the same target (i.e. such that the resulting protein, polypeptide or other compound or molecule is a bi- or multiparatopic construct).

The invention further relates to a method as further described herein, in which said protein, polypeptide or other compound or molecule comprises or essentially consists of two immunoglobulin single variable domains (either linked directly or via a suitable linker).

The invention further relates to a method as further described herein, in which said protein, polypeptide or other compound or molecule comprises or essentially consists of three immunoglobulin single variable domains (either linked directly or via a suitable linker).

The invention further relates to a method as further described herein, in which said protein, polypeptide or other compound or molecule comprises or essentially consists of four immunoglobulin single variable domains (either linked directly or via a suitable linker).

The invention further relates to a method as further described herein, in which said protein, polypeptide or other compound or molecule further comprises at least one moiety, binding domain or binding unit that confers an increased half-life to said protein, polypeptide or other compound or molecule (i.e. compared to the corresponding protein, polypeptide or other compound or molecule without said moiety, binding domain or binding unit).

The invention further relates to a method as further described herein, in which said at least one moiety, binding domain or binding unit that confers an increased half-life to said protein, polypeptide or other compound or molecule is an immunoglobulin single variable domain.

The invention further relates to a method as further described herein, in which said at least one moiety, binding domain or binding unit that confers an increased half-life to said protein, polypeptide or other compound or molecule is an immunoglobulin single variable domain that is directed against a serum protein, and in particular against a human serum protein.

The invention further relates to a method as further described herein, in which said at least one moiety, binding domain or binding unit that confers an increased half-life to said protein, polypeptide or other compound or molecule is an immunoglobulin single variable domain that is directed against serum albumin, and in particular against human serum albumin.

The invention further relates to a method as further described herein, in which said at least one moiety, binding domain or binding unit that confers an increased half-life to said protein, polypeptide or other compound or molecule is a nanobody, dAb or a (single) domain antibody.

The invention further relates to a method as further described herein, in which said at least one moiety, binding domain or binding unit that confers an increased half-life to said protein, polypeptide or other compound or molecule is a nanobody, and in particular a nanobody that is directed against a serum, protein (and in particular a human serum protein) and in particular against serum albumin (and more in particular against human serum albumin).

The invention further relates to a method as further described herein, in which said protein, polypeptide or other compound or molecule comprises or essentially consists of at least two (such as two, three, four or five) immunoglobulin single variable domains (either linked directly or via a suitable linker), at least one of which is directed against a serum protein, and in particular against a human serum protein.

The invention further relates to a method as further described herein, in which said protein, polypeptide or other compound or molecule comprises or essentially consists of at least two (such as two, three, four or five) immunoglobulin single variable domains (either linked directly or via a suitable linker), at least one of which is directed against serum albumin, and in particular against human serum albumin (which may be at the N-terminal end, at the C-terminal end, or if the compound in total (i.e. including the serum albumin-binding ISVD) comprises more than three ISVDs, somewhere in the middle of the compound).

The invention further relates to a method as further described herein, in which the at least one immunoglobulin single variable domain that is directed against a serum protein (and in particular against a human serum protein) and in particular against serum albumin (and more in particular against human serum albumin) has an exposed C-terminal end/region (i.e. is the at least one immunoglobulin variable domain with an exposed C-terminal end/region that is present in the protein, polypeptide or other compound or molecule).

The invention further relates to a method as further described herein, in which the at least one immunoglobulin single variable domain that is directed against a serum protein (and in particular against a human serum protein) and in particular against serum albumin (and more in particular against human serum albumin) is present at and/or forms the C-terminal end/region of said protein, polypeptide or other compound or molecule.

The invention further relates to a method as further described herein, in which the C-terminal end/region of the at least one immunoglobulin single variable domain that is directed against a serum protein (and in particular against a human serum protein) and in particular against serum albumin (and more in particular against human serum albumin) has the sequence VTVSS (i.e. the last 5 C-terminal amino acid residues of said immunoglobulin variable domain are VTVSS).

The invention further relates to a method as further described herein, in which said protein, polypeptide or other compound or molecule comprises or essentially consists of either:

two immunoglobulin single variable domains (either linked directly or via a suitable linker), i.e. (said) one immunoglobulin single variable domain (such as a nanobody) that confers an increased half-life and one other immunoglobulin single variable domain (such as a nanobody) that may in particular be directed against a therapeutic target three immunoglobulin single variable domains (either linked directly or via a suitable linker), i.e. (said) one immunoglobulin single variable domain (such as a nanobody) that confers an increased half-life and two other immunoglobulin single variable domains (such as two other nanobodies) that may in particular be directed against a therapeutic target (in which said two other immunoglobulin single variable domains may be directed against the same target, against two different targets or against two different epitopes on the same target); or four or five immunoglobulin single variable domains (either linked directly or via a suitable linker), i.e. (said) one immunoglobulin single variable domain (such as a nanobody) that confers an increased half-life and three or four other immunoglobulin single variable domains (such as three of four other nanobodies) that may in particular be directed against a therapeutic target (in which said three or four other immunoglobulin single variable domains may be directed against the same target, against different targets and/or against different epitopes on the same target, or any combination thereof).

The invention further relates to a method as further described herein, in which either the detection agent or the capturing agent has the amino acid sequence VTVSS(X)$_n$ (SEQ ID NO:XXX) at its C-terminal end, in which n is 1 to 10, preferably 1 to 5, such as 1, 2, 3, 4 or 5 (and preferably 1 or 2, such as 1), and in which each X is an (preferably naturally occurring) amino acid residue; and in which each X is independently chosen, and preferably independently chosen from the group consisting of alanine (A), glycine (G), valine (V), leucine (L) or isoleucine (I).

The invention further relates to a method as further described herein, in which the capturing agent and the detection agent have essentially the same amino acid sequence as the protein, polypeptide or other compound or molecule, but with 1 to 10, preferably 1 to 5 (such as 1, 2, 3, 4 or 5) amino acid residues (independently chosen, and preferably independently chosen from the group consisting of alanine (A), glycine (G), valine (V), leucine (L) or isoleucine (I)) added at the C-terminal end of either the capturing agent or the detection agent.

The invention further relates to a method as further described herein, in which the protein, polypeptide or other compound or molecule has the amino acid sequence VTVSS at its C-terminal end and in which either the detection agent or the capturing agent has the amino acid sequence VTVSS (X)$_n$ (SEQ ID NO:XXX) at its C-terminal end, in which n is 1 to 10, preferably 1 to 5, such as 1, 2, 3, 4 or 5 (and preferably 1 or 2, such as 1), and in which each X is an (preferably naturally occurring) amino acid residue that is independently chosen, and preferably independently chosen from the group consisting of alanine (A), glycine (G), valine (V), leucine (L) or isoleucine (I).

The invention further relates to a method as further described herein, in which the detectable tag or label comprised within the detection agent is a tag or label that can be detected using electrochemiluminescence or other suitable techniques (e.g. Delfia®, Luminex®, FRET or other suitable detectable tags/detection techniques for use with Elisa-based ligand-binding assays.

BRIEF DESCRIPTION OF THE DRAWINGS

The invention will now be illustrated by means of the following non-limiting examples and Figures, in which:

FIG. 5 is a table summarizing the different assay formats that were compared in Example 1.

Experimental Part

EXAMPLE 1

Figure 1:
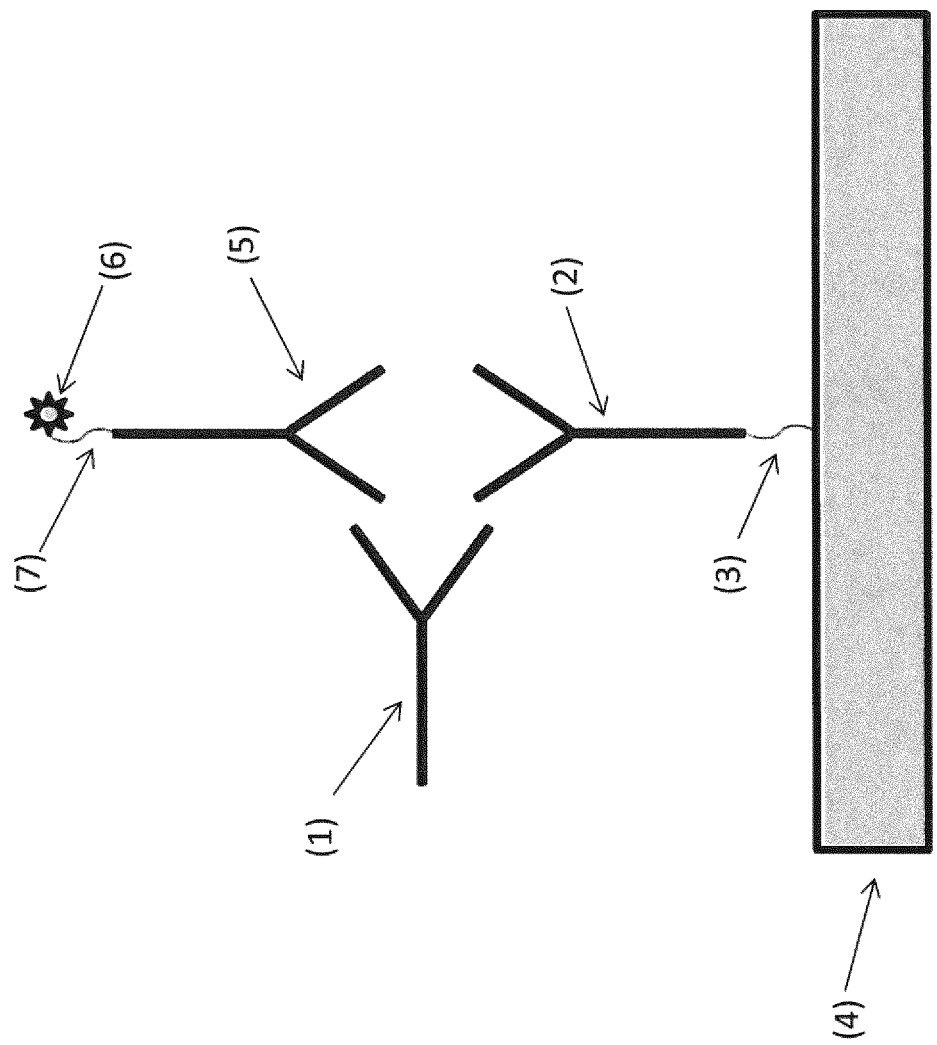
FIG. 1 schematically shows the principles of prior art bridging assay formats (such as ELISA-bridging format or ECL bridging format) for detecting ADA's against a conventional antibody.
Figure 2A:
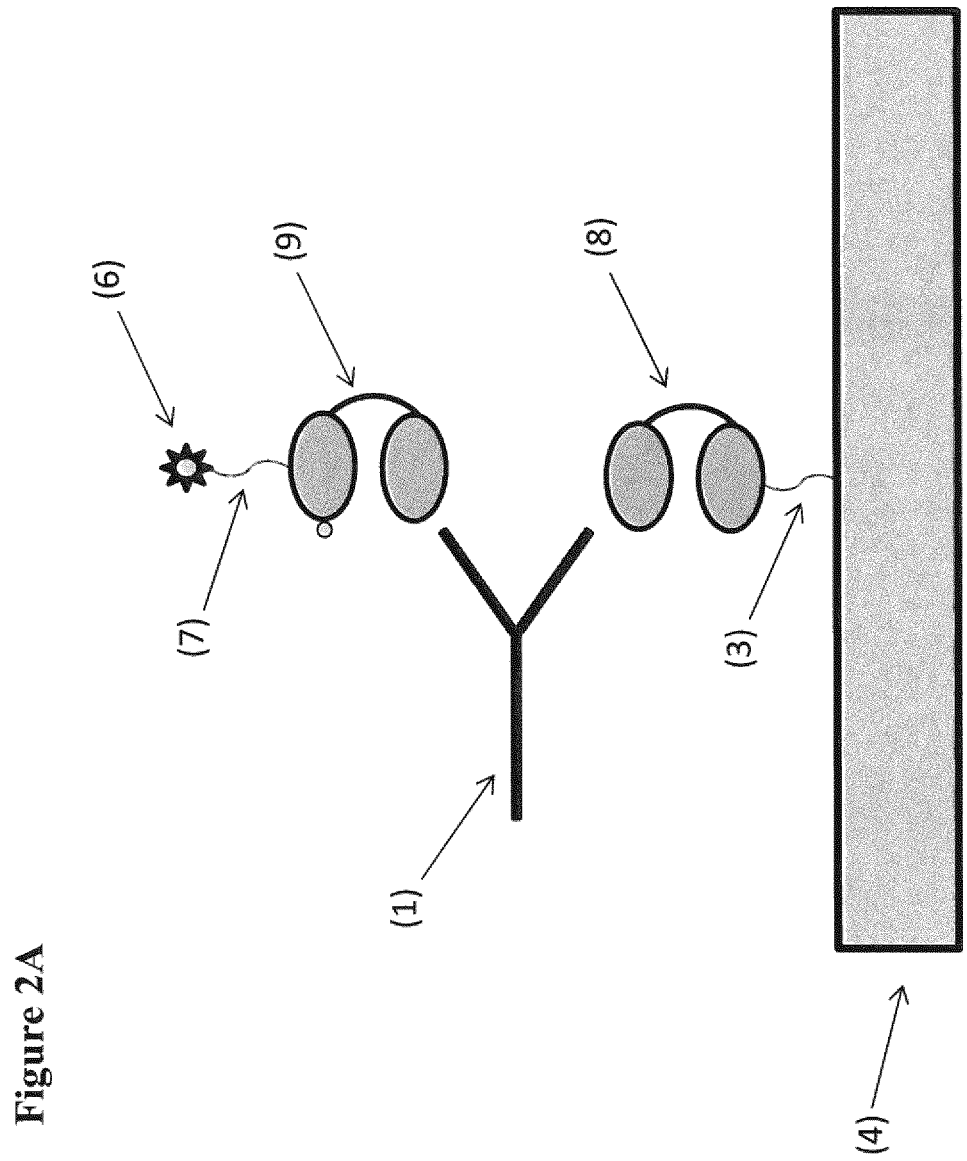
FIGS. 2A to 2D schematically show the use of an assay of the invention for detecting ADA's against a bivalent ISV construct, using an alanine-extended detection agent.
Figure 2C:
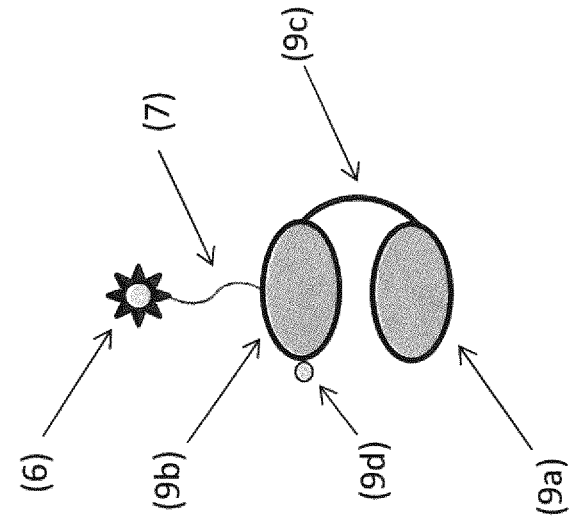
Figure 2B:
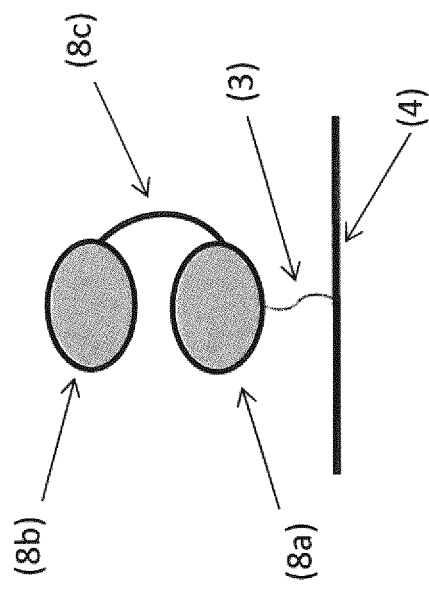
Figure 2D:
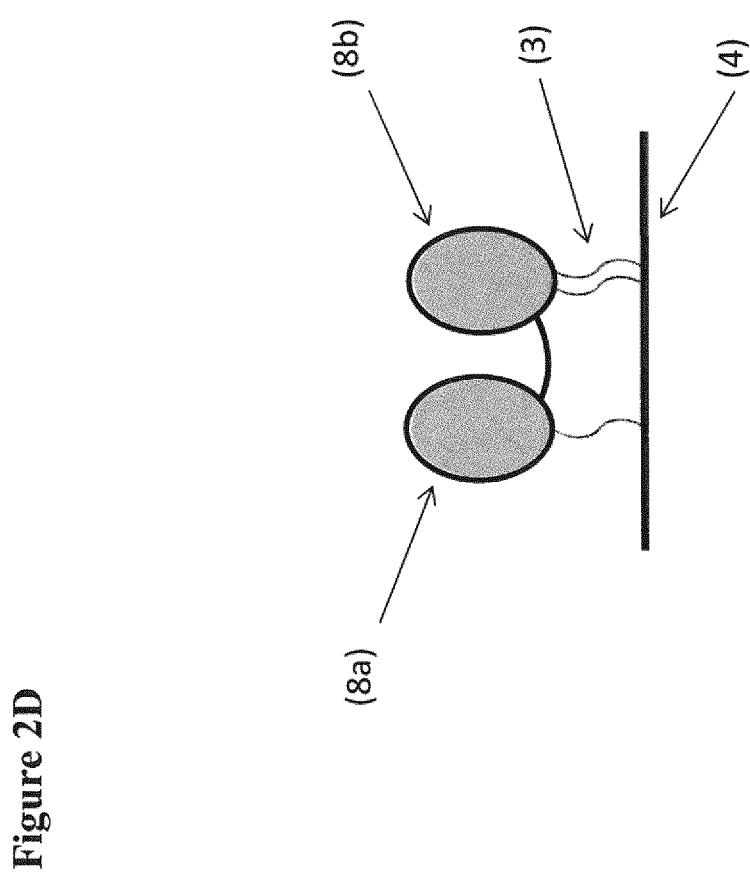
Figure 3:
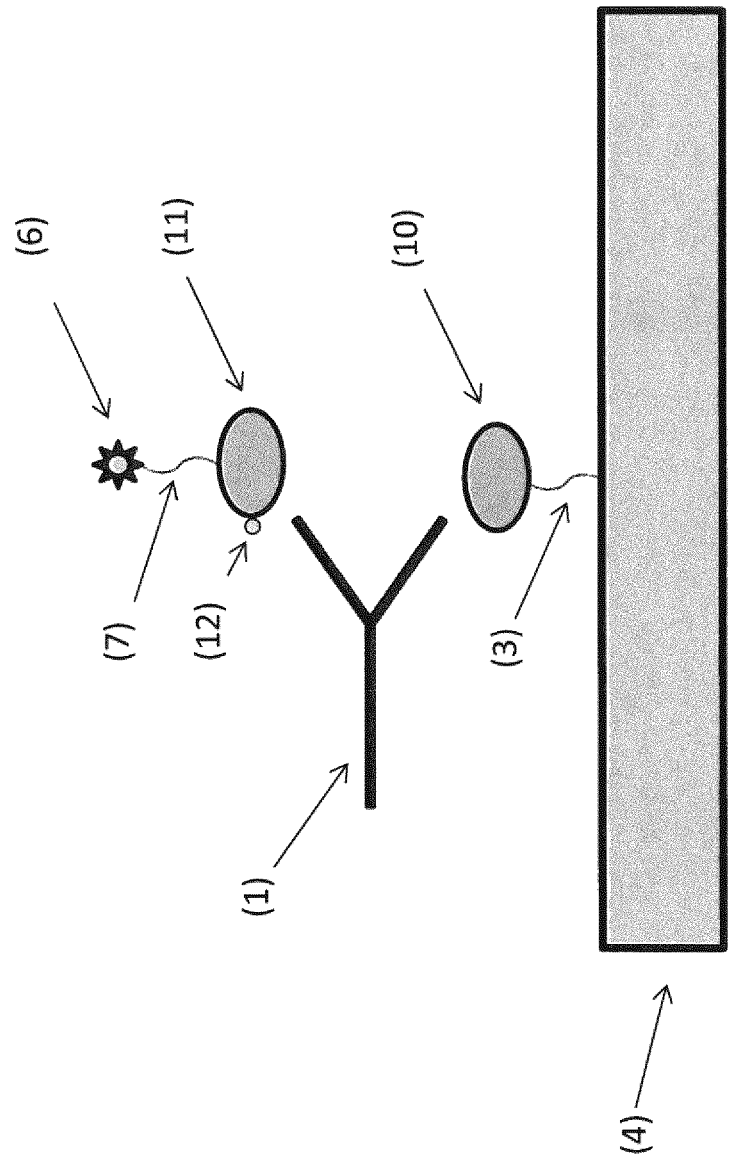
FIG. 3 schematically show the use of an assay of the invention for detecting ADA's against a monovalent ISV.
Figure 4A:
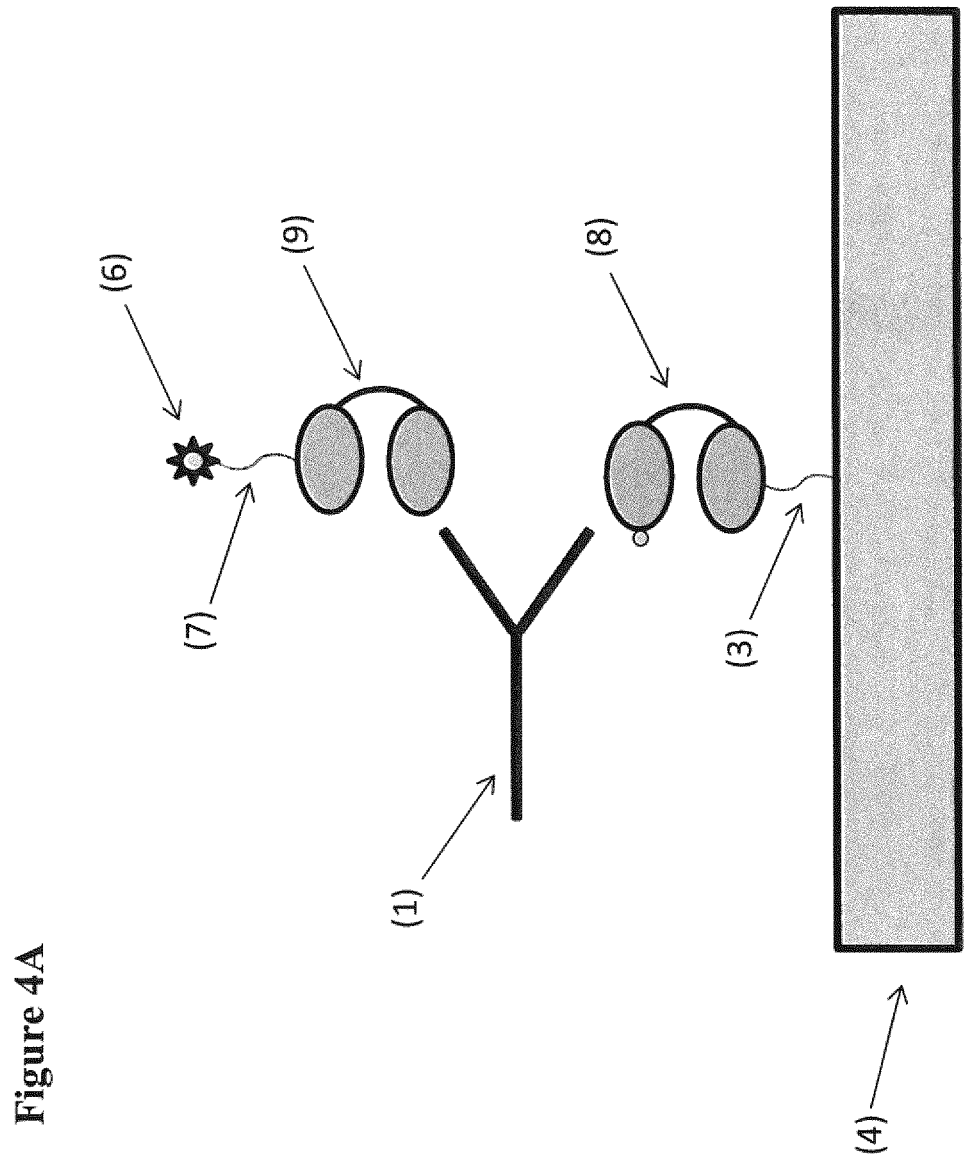
FIGS. 4A to 4C schematically show the use of an assay of the invention for detecting ADA's against a bivalent ISV construct, using an alanine-extended capturing agent.
Figure 4C:
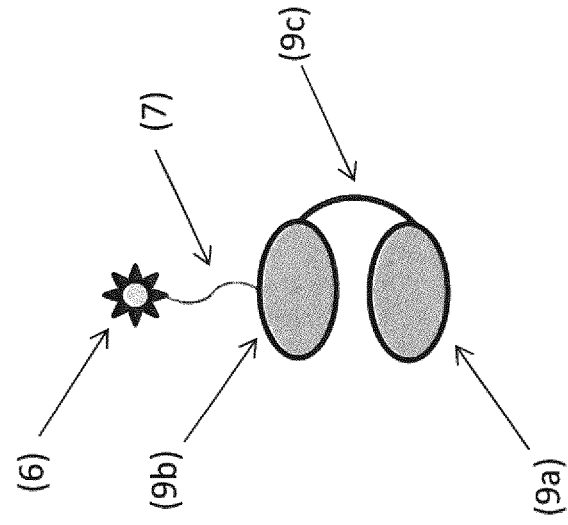
Figure 4B:
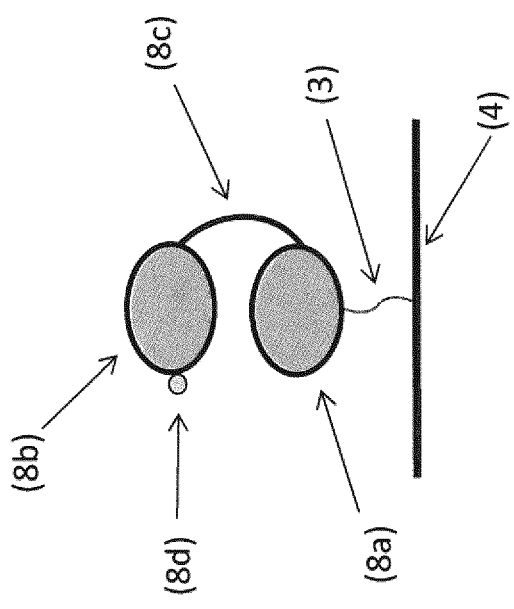

Comparison of Different Assay Formats 5 different ADA assay formats for detecting ADA's (schematically shown in FIG. 5) were evaluated for the impact of protein interference on the respective assay performance (when used for measuring ADA's against a Nanobody), using a set of 171 test samples comprised of plasma or serum samples from 121 healthy volunteers and 50 rheumatoid arthritis patients (none of whom had previously been exposed to Nanobodies). The Nanobody-based protein used was SEQ ID No. 417 from WO06/122786.

Each of the assay formats was evaluated on the prevalence and magnitude of interference in the respective assays as well as the impact of any interference on assay performance, including screening and confirmatory cut-point setting, assay sensitivity and the extent to which it was possible to reliably detect treatment emergent ADA in presence of interference.

It was found that the modified ECL-based bridging format provided/allowed for: (i) assay sensitivity of less than 500 ng/ml, as recommended by the applicable guidelines for ADA assays: (ii) suitable cut-point setting (both screening and confirmatory) using appropriate statistics, again as recommended by standard guidelines for ADA assays; and (iii) even relatively low amounts of "true" ADA's could be detected in samples tested that (also) contained interfering factors (it is also expected that detection of treatment-emergent ADA's will still be possible at relatively high levels of interfering factors, although at very high levels sensitivity may be (somewhat) reduced All other four assay formats were impacted to a much larger degree by interference, such that detection of ADA was severely impeded in the majority of interference containing samples. Only in samples presenting low/very low levels of interference, could ADA's be reliably detected.

The amount of ADA that could be detected is further dependent on the sensitivity of the assay: the sequential ECL based bridging format demonstrated the lowest sensitivity (estimated to be more than 5 μg/ml), whereas the sequential ELISA-based bridging format and the direct ELISA format were found to have a sensitivity estimated to be 600 ng/ml, which is higher than the sensitivity recommended by applicable guidelines. Also, for all assay formats tested, it was found that there is a certain degree of correlation between the level of interference (or baseline ECL signal) and the amount of ADA that can be detected. This can make it possible to define threshold values (based on ECL read outs) for maximum interference levels at which low levels of ADA's can still be reliably detected.

The results are also summarized in Table 1.

TABLE 1 overview of different assay format evaluated for impact of interference on assay performance.

| ADA assay format | Sensitivity (+IF) | Cut-point setting (+IF) | Detection of est. 620 ng/ml pAb positive control |
|---|---|---|---|
| Homogenous ECL-based bridging assay | OK | Not OK | Not OK |
| Sequential ECL-based bridging assay | Not OK | OK | Not OK |
| Sequential ELISA-based bridging assay | Not OK | Not OK | Not OK |
| Direct ELISA | Not OK | Not OK | Technically not feasible |
| Homogenous ECL-based modified bridging assay | OK | OK | OK |

EXAMPLE 2

Comparison of Homogeneous ECL-Based Bridging Format Using a C-Terminally Modified Detection Agent With a Homogeneous ECL-Based Bridging Format Using a Non-Modified Detection Agent Two homogeneous ECL-based bridging formats were compared. In one format, the capturing agent (biotinylated for binding to the support) and the detection agent (sulfo-tagged for ECL detection) had essentially the same sequence (SEQ ID NO. 417 from WO 06/122786). In the other format, the same capturing agent and detection agent were used as were used for the first format, but the detection agent had been modified by adding one additional alanine residue to the C-terminus of the Nanobody-based protein sequence.

The same 171 test samples used in Example 1 were again tested in a screening and confirmatory set up.

Figure 6:
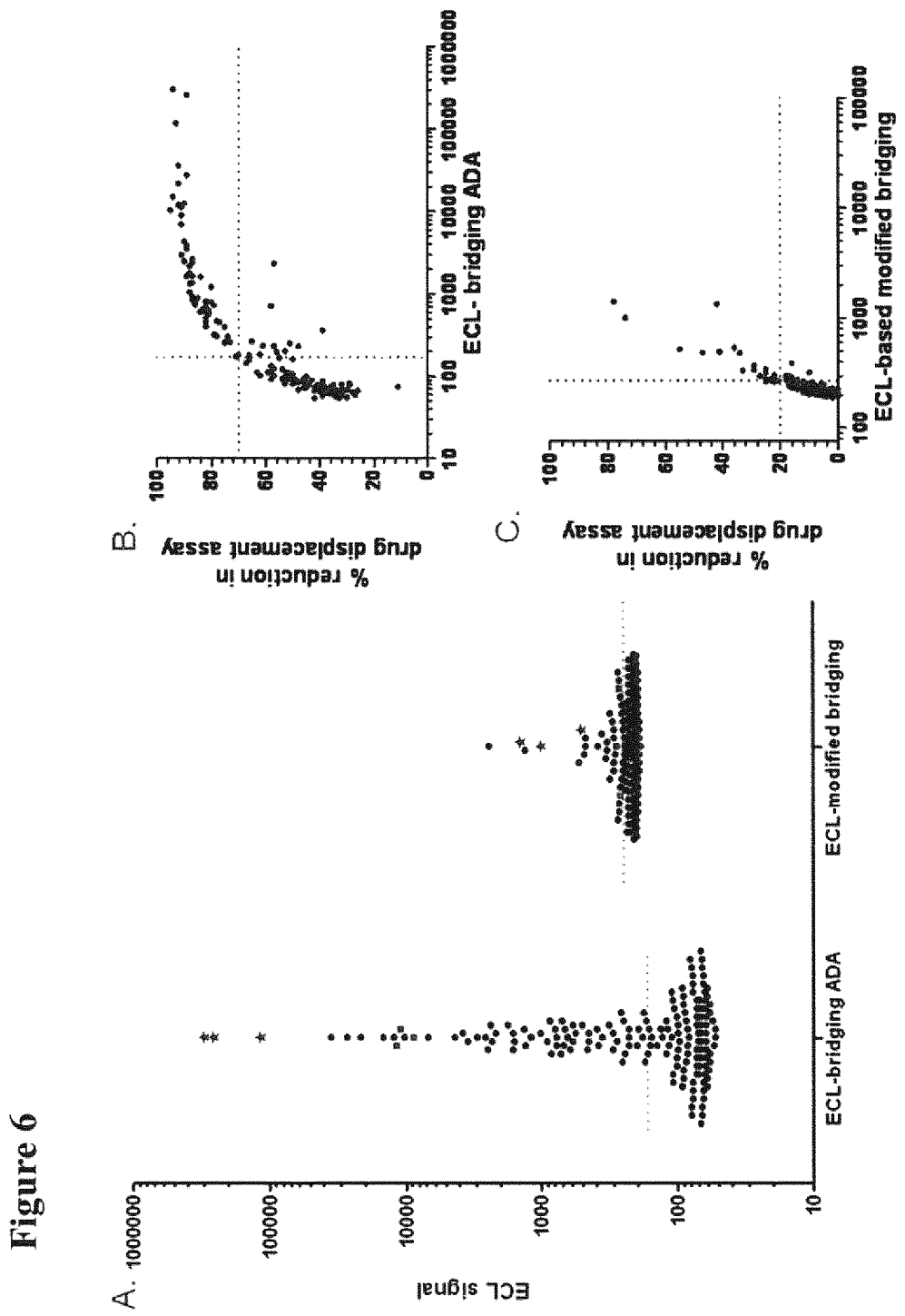
FIG. 6 shows the screening and confirmatory results of 171 test samples obtained in Example 2 for a conventional homogeneous ECL based bridging format (prior art) and the modified bridging format of the invention using an alanine-extended detection agent.

When the homogeneous modified bridging format according to the invention was used, it was found that the number of test samples presenting high ECL signals was greatly reduced (FIG. 6). Furthermore, variation in ECL-signals is less; varying from 180 to <2,500. A commonly used statistical method (box plot analysis for outlier identification) could be used to successfully define cut-points on the screening and confirmatory data set.

Panel A in FIG. 6 shows the screening results of the 171 test samples in both assay formats. Screening cut-points are indicated by dotted lines. Representative samples having high interference levels in the homogeneous ECL-based bridging assay (which samples were also used in experiments referred to in Example 1) are indicated by stars or squares respectively, with all other samples being indicated by dots.

Panel B in FIG. 6 shows results of the confirmatory set up compared to screening values of the homogeneous ECL-based bridging assay: screening results (ECL signal) were plotted versus the % reduction obtained in the confirmatory assay. A positive correlation is found between the screening ECL signal and % reduction obtained in the confirmatory assay.

The obtained confirmatory results show a continuous distribution (i.e., % reduction varies from <20% to >90% reduction), indicating that the interference is present in varying amounts in many test samples. This makes it difficult to define a distinct interference-negative population which is a prerequisite for commonly used statistical methods defining screening and confirmatory cut-points. As screening and confirmatory cut-point setting is based on the 95th percentile/confidence interval and 99th percentile/confidence interval, respectively, of the response of the blank, non-treated population, the calculated cut-point will be highly dependent on the distribution of the ECL signals within the validation sample set and therefore cut-point setting becomes arbitrary.

Panel C in FIG. 6 shows results from screening and confirmatory results in the modified bridging format (i.e. using an alanine-extended detection agent): screening results (ECL signal) were plotted versus the % reduction obtained in the confirmatory assay. The number of test samples showing high screening ECL values is lower, allowing cut-point setting via commonly used statistical methods.

The data from FIG. 6 shows that whereas a conventional ECL bridging format is significantly impacted by interference, the modified bridging assay using an alanine-extended capturing agent is impacted to a far lesser extent. Also, whereas for a conventional bridging ADA assay format the setting of the cut point would to a large extent be more or less arbitrary, relevant cut points could be set for the modified bridging ADA format using commonly used statistical methods.

Figure 7:
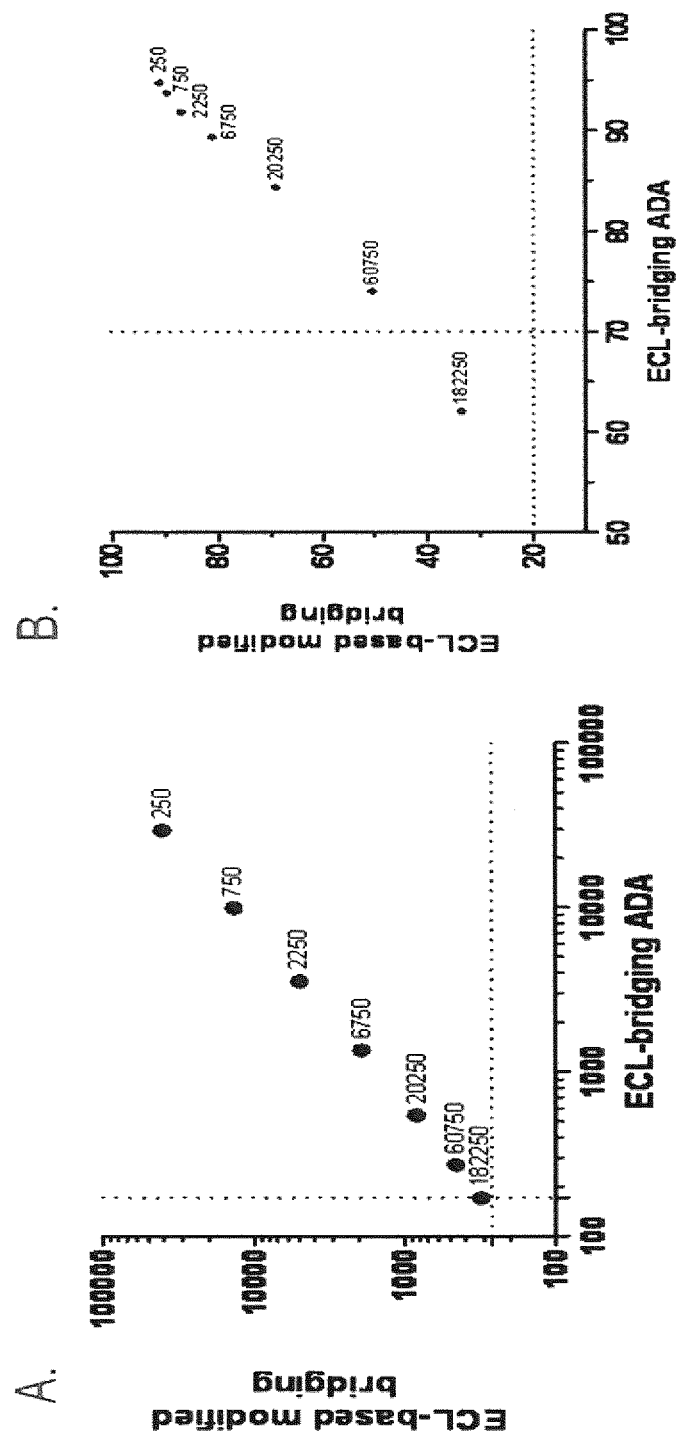
FIG. 7 shows a comparison of the conventional homogeneous ECL-based bridging format with the modified homogeneous ECL-based bridging format in the absence of pre-existing antibodies.
Figure 8:
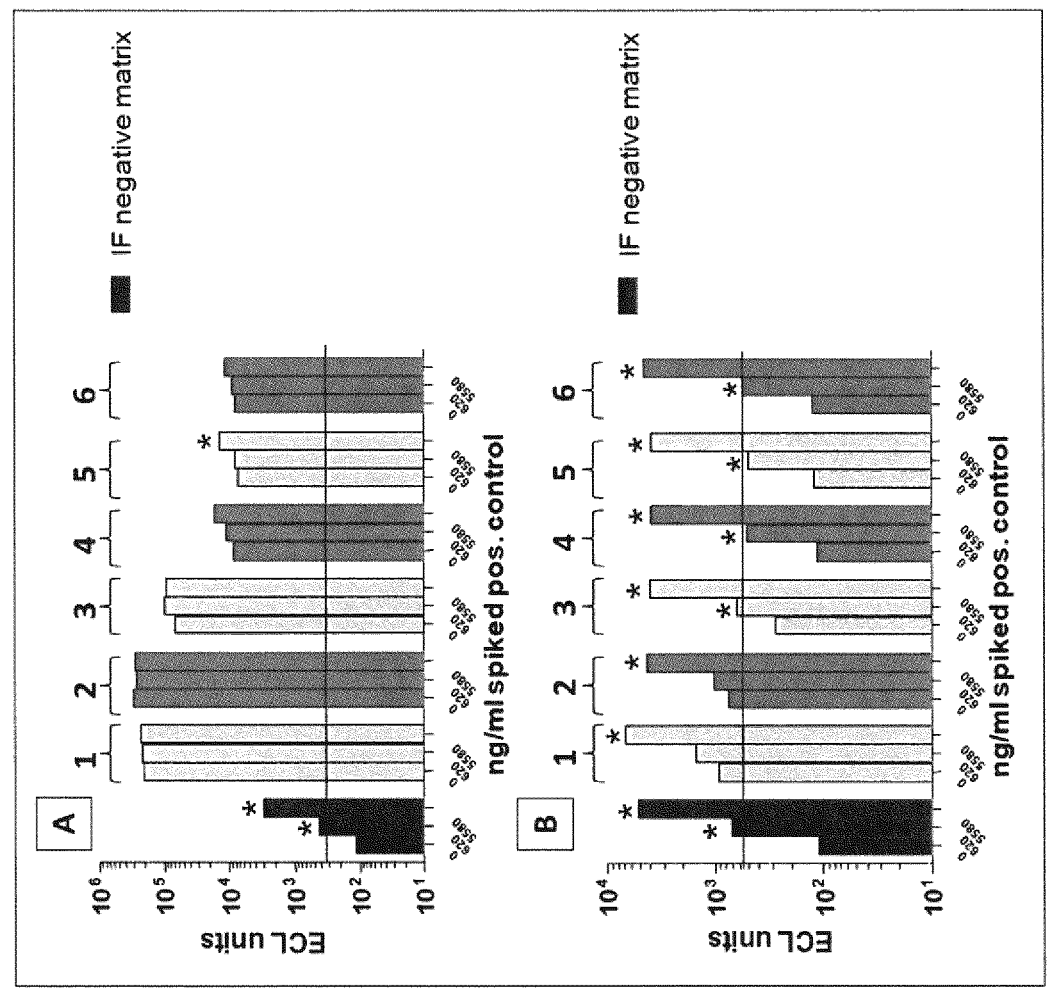
FIG. 8 shows the result of a comparative evaluation of the impact of interference on detection of ADA in a conventional bridging ADA assay versus the modified bridging ADA assay. The graphs show the detection of spiked positive control in interference containing samples, for both the conventional assay (Panel A) and the modified assay (Panel B).

The results above were further confirmed by a separate experiment in which different test samples with varying interference levels were spiked with the rabbit positive control serum used to obtain the data shown in FIG. 7 and were evaluated in both assay formats (results shown in FIG. 8). Again, it was found that for the conventional bridging assay format, it was not possible to (reliably) detect ADA's in samples with high interference level; whereas for the modified bridging format involving the use of an alanine-extended capturing agent it was found that this assay could successfully detect low amounts of ADA in the presence of interference (see the data shown in FIG. 8). The bars indicate the ECL signal of different matrix samples spiked with positive control polyclonal serum spiked at concentrations of 0 and 620 and 5580 ng/ml. The black bars represent results obtained with interference-negative matrix. The gray bars numbered 1-6 depict ECL signals of the positive control pAb spiked at 3 different concentrations into example samples containing varying amounts of interference. Panel A shows the results obtained in the homogeneous bridging assay and panel B the results obtained in the homogeneous modified bridging assay. The black horizontal line shows an example of suitable threshold ECL values for each of these assays, i.e. the ECL value of the test sample that still allows detection of an acceptable amount of ADA in the presence of interference).

SEQUENCE LISTING

```
<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: C-terminal sequence

<400> SEQUENCE: 1

Val Thr Val Ser Ser
1               5

<210> SEQ ID NO 2
<211> LENGTH: 6
<212> TYPE: PRT
<213> ORGANISM: Artificial Sequence
<220> FEATURE:
<223> OTHER INFORMATION: C-terminal sequence
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is cho
      sen independently from any amino acids

<400> SEQUENCE: 2

Val Thr Val Ser Ser Xaa
1               5
```

Also, the sensitivity of both assay formats in the absence of interference was compared, using data obtained for a positive control serum (rabbit serum raised against SEQ ID NO. 417 from WO06/122786) as a reference. In the absence of interference, the sensitivity of both assays was comparable as is shown in FIG. 7. This confirms that the differences between the two assay formats in the presence of interference are indeed due to the presence of the interference.

The invention claimed is:

1. Method for detecting and/or measuring in a sample anti-drug antibodies that bind to a polypeptide that comprises at least one variable domain of the heavy chain of a heavy-chain antibody (VHH domain), humanized VHH domain, or camelized heavy chain variable domain of a conventional antibody (VH domain) with an exposed C-terminal region with the sequence VTVSS (SEQ ID NO: 1), said method comprising at least the steps of:

a) contacting said sample with a capturing agent that is immobilized on a support, wherein said capturing agent is or essentially consists of said polypeptide, under conditions such that anti-drug antibodies against said polypeptide can bind to said capturing agent to form a complex of the capturing agent and any captured anti-drug antibodies;

b) optionally removing any components or constituents present in said sample that do not bind to the capturing agent;

c) detecting or measuring any anti-drug antibodies that have bound to the capturing agent, by contacting the complex of the capturing agent and the captured anti-drug antibodies with a detection agent, under conditions such that said detection agent can bind to the complex of the capturing agent and the captured anti-drug antibodies, wherein said detection agent is or essentially consists of: (i) said polypeptide; (ii) a detectable tag or label bound to said polypeptide either directly or via a suitable linker and (iii) 1-5 amino acid residues that are linked to the exposed C-terminal end with sequence VTVSS (SEQ ID NO: 1) of the VHH domain, humanized VHH domain, or camelized VH domain, in which said sample is a sample of whole blood, serum, plasma, ocular fluid, bronchoalveolar fluid/bronchoalveolar lavage fluid (BALF), cerebrospinal fluid or another biological fluid.

2. Method according to claim 1, in which the detection agent has the amino acid sequence VTVSS(X)$_n$(SEQ ID NO:2) at its C-terminal end, in which n is 1 to 5; and in which each X is a naturally-occurring amino acid residue that is independently chosen.

3. Method according to claim 1, in which the sample has been obtained from a subject to which said polypeptide has been administered and wherein the polypeptide has been administered to a subject according to a regimen that is such that there is a risk or possibility that anti-drug antibodies against the polypeptide have been raised in the subject to which said polypeptide has been administered.

4. Method according to claim 1, in which the polypeptide has a half-life of at least 1 day in a human subject.

5. Method according to claim 1, in which the VHH domain, humanized VHH domain, or camelized VH domain with the exposed C-terminal region with the sequence VTVSS (SEQ ID NO: 1) is present at the C-terminal end of said polypeptide.

6. Method according to claim 1, in which the detectable tag or label comprised within the detection agent is a tag or label that can be detected using electrochemiluminescence techniques.

7. Method according to claim 2, wherein each X is independently chosen from the group consisting of alanine (A), glycine (G), valine (V), leucine (L) or isoleucine (I).

* * * * *